(12) United States Patent
Carson et al.

(10) Patent No.: US 11,821,726 B2
(45) Date of Patent: *Nov. 21, 2023

(54) MOBILE TURF INSTRUMENT APPARATUS

(71) Applicant: THE TORO COMPANY, Bloomington, MN (US)

(72) Inventors: Troy D. Carson, Richfield, MN (US); Chris A. Wadzinski, Inver Grove Heights, MN (US); Jackie R. Gust, Northfield, MN (US)

(73) Assignee: The Toro Company, Bloomington, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/728,686

(22) Filed: Apr. 25, 2022

(65) Prior Publication Data
US 2022/0357154 A1 Nov. 10, 2022

Related U.S. Application Data

(63) Continuation of application No. 16/474,295, filed as application No. PCT/US2018/013478 on Jan. 12, 2018, now Pat. No. 11,320,261.

(Continued)

(51) Int. Cl.
*G01B 21/20* (2006.01)
*A01B 39/12* (2006.01)
(Continued)

(52) U.S. Cl.
CPC ............... *G01B 21/20* (2013.01); *A01B 39/12* (2013.01); *G01B 21/30* (2013.01); *G01N 33/24* (2013.01)

(58) Field of Classification Search
CPC .......... G01B 21/20; G01B 21/30; G01B 5/20; G01B 3/12; G01B 5/18; A01B 39/12; G01N 33/24; E01C 19/15; E01C 23/07
See application file for complete search history.

(56) References Cited

U.S. PATENT DOCUMENTS 3,862,496 A 1/1975 Rysti et al.
5,549,412 A 8/1996 Malone
(Continued)

FOREIGN PATENT DOCUMENTS

CA 288936 * 10/2015 ............. E01C 13/08
CN 204478986 U 7/2015
(Continued)

OTHER PUBLICATIONS

EPO, "Extended European Search Report and Opinion" (dated Dec. 8, 2020).

(Continued)

*Primary Examiner* — Tung S Lau
(74) *Attorney, Agent, or Firm* — Merchant & Gould P.C.

(57) ABSTRACT

A probe assembly for measuring a synthetic turf infill profile having a probe, a turf surface contact assembly and a sensor. The probe is configured to extend down through the turf infill profile until a tip of the probe contacts a lower boundary of the turf infill profile. The surface contact assembly is vertically movable relative to the probe while the probe is being moved downwardly into the turf infill profile, wherein the surface contact assembly has a contact area with the turf surface that is large enough to retain the surface contact assembly resting atop an upper boundary of the turf infill profile when the lowermost tip of the at least one probe has contacted the lower boundary of the turf infill profile. The sensor reads the distance between the upper and lower boundaries of the turf infill profile at a sampled location in the turf surface.

16 Claims, 20 Drawing Sheets

Related U.S. Application Data

(60) Provisional application No. 62/445,577, filed on Jan. 12, 2017.

(51) Int. Cl.
    *G01B 21/30*    (2006.01)
    *G01N 33/24*    (2006.01)

(56) References Cited

U.S. PATENT DOCUMENTS

| | | | |
|---|---|---|---|
| 5,864,059 A | 1/1999 | Sturm et al. | |
| 7,357,966 B2 * | 4/2008 | Dipple | E01C 13/08 428/17 |
| 7,628,059 B1 | 12/2009 | Scherbring | |
| 9,010,450 B2 | 4/2015 | Motz et al. | |
| 9,308,557 B2 * | 4/2016 | Nicholls | B07B 11/08 |
| 9,572,416 B2 | 2/2017 | Pizano et al. | |
| 11,021,842 B2 | 6/2021 | Sawyer | |
| 11,320,261 B2 * | 5/2022 | Carson | E01C 19/15 |
| 2006/0045994 A1 * | 3/2006 | Dipple | E01C 13/02 428/17 |
| 2006/0045995 A1 * | 3/2006 | Dipple | E01C 13/02 428/17 |
| 2007/0009680 A1 * | 1/2007 | Dipple | E01C 13/02 428/17 |
| 2007/0224361 A1 * | 9/2007 | Bissonnette | A63C 19/08 239/11 |
| 2009/0015056 A1 | 1/2009 | Hall et al. | |
| 2010/0151158 A1 * | 6/2010 | Mashburn | C08L 23/12 428/17 |
| 2010/0166984 A1 | 7/2010 | Nusca | |
| 2011/0203356 A1 | 8/2011 | Scherbring | |
| 2012/0315816 A1 | 12/2012 | Fowler et al. | |
| 2013/0078394 A1 | 3/2013 | Taylor | |
| 2013/0180440 A1 * | 7/2013 | Hall | D05C 15/16 112/80.32 |
| 2013/0330156 A1 | 12/2013 | Motz et al. | |
| 2015/0224675 A1 | 8/2015 | Madhburn et al. | |
| 2015/0298357 A1 * | 10/2015 | Mashburn | B29B 9/06 428/17 |
| 2015/0308056 A1 | 10/2015 | Spittle et al. | |
| 2017/0175343 A1 | 6/2017 | des Garennes et al. | |
| 2018/0347121 A1 * | 12/2018 | Mashburn | D05C 17/02 |
| 2018/0371708 A1 | 12/2018 | Spittle et al. | |

FOREIGN PATENT DOCUMENTS

| | | | |
|---|---|---|---|
| EP | 2917413 A2 * | 9/2015 | E01C 13/08 |
| JP | H7-79681 A | 3/1995 | |
| KR | 20080051957 A | 6/2008 | |
| WO | WO 2013/012710 A * | 1/2013 | B07B 15/00 |
| WO | 2014/007627 A1 | 1/2014 | |
| WO | WO 2015/109373 A1 * | 7/2015 | E01H 1/0863 |
| WO | WO 2018/132650 A1 * | 7/2018 | E01C 19/15 |
| WO | WO 2019/215768 A1 * | 11/2019 | E01C 13/08 |

OTHER PUBLICATIONS

EPO, "Supplementary Partial European Search Report and Accompanying Opinion" (dated Jul. 17, 2020).

Turf-Tec International, "Turf-Tec Professional Model Infill Depth Gauge For Synthetic Turf" brochure, admitted prior art.

Sports Turf Magazine, "Advice On Maintaining The Infill On Your Synthetic Field" article (Jul. 2014).

KIPO, "Written Opinion Of The International Searching Authority" (dated Apr. 20, 2018).

* cited by examiner

MOBILE TURF INSTRUMENT APPARATUS

CROSS-REFERENCE TO RELATED APPLICATIONS

This is a Continuation of U.S. patent application Ser. No. 16/474,295, filed Jun. 27, 2019, now U.S. Pat. No. 11,320,061; Which is a U.S. National Stage Application of PCT/US2018/13478, filed Jan. 12, 2018; which claims benefit of priority to U.S. Provisional Application No. 62/445,577, filed. Jan. 12, 2017, which applications are incorporated herein by reference. To the extent appropriate, a claim of priority is made to each of the above-disclosed applications.

TECHNICAL FIELD

This invention relates generally to the field of turf maintenance equipment. More particularly, this invention relates to equipment carrying instruments for measuring a profile depth and applying a variable rate top dressing.

BACKGROUND OF THE INVENTION

The turf maintenance field involves a wide range of equipment used to promote a uniform surface, on both natural and synthetic turf. For example, top-dressing equipment is used to apply particulate on both natural and synthetic turf. Grooming devices are used to move and smooth particulate on both natural and synthetic turf. Irrigation systems are used to settle the particulate in both natural and synthetic turf.

In order to determine the particulate depth in synthetic turf, a hand probe is often inserted into the synthetic turf profile. However, a hand probe requiring insertion into the profile makes for a difficult and tiring task. Moreover, when measuring the particulate depth over a large area of synthetic turf, such as a soccer field, it is extremely time consuming and laborious, often yielding inconsistent results.

Maintaining a uniform surface on a natural or synthetic turf field also presents a unique difficulty. Laser level grading equipment is sometimes used to establish a uniform surface prior to seeding, sodding or installation. However, once turf exists, traditional grading equipment is no longer suitable as turf damage may occur.

SUMMARY

One aspect of the present invention relates to a probe assembly for measuring a turf infill profile of a synthetic turf surface, which comprises at least one probe, a turf surface contact assembly, and a sensor. The at least one probe is configured to extend down through the turf infill profile until a lowermost tip of the at least one probe contacts a backing material comprising a lower boundary of the turf infill profile. The turf surface contact assembly is vertically movable relative to the at least one probe while the at least one probe is being moved downwardly into the turf infill profile, wherein the turf surface contact assembly is vertically movable relative to the lowermost tip of the at least one probe and has a contact area with the turf surface that is large enough to retain the turf surface contact assembly resting atop an upper boundary of the turf infill profile when the lowermost tip of the at least one probe has contacted the lower boundary of the turf infill profile. The sensor reads the distance between the upper and lower boundaries of the turf infill profile at a sampled location in the turf surface.

In another aspect, the present invention relates to a mobile turf instrument apparatus for measuring a synthetic turf infill profile, which comprises a frame, an arm, an assembly, and a sensor. The frame is supported for movement over the surface. The arm is carried on the frame for rotation about a first substantially horizontal axis of rotation and the arm may repeatedly and cyclically rotate about the first axis of rotation as the frame is moved over the surface. The assembly is carried on the arm for rotation about a second substantially horizontal axis of rotation and the assembly rotates in a direction that is opposite to a direction in which the arm rotates such that the assembly is self-leveling on the arm. The assembly is configured to engage with the surface during each cycle of rotation of the arm. The sensor is carried on the assembly for measuring the vertical distance of an infill profile.

In still another aspect, the present invention relates to a mobile turf instrument apparatus for measuring a turf profile, which comprises a frame, a measurement apparatus, a computer, a variable rate particulate application device, and a control system. The frame is supported for movement over a surface. The measurement apparatus is carried on the frame for measuring the vertical distance between an upper profile position and a lower profile position. The computer has a central processing unit, a memory coupled to the central processing unit and an electronic interface coupled between the instrument assembly and the memory for transferring the measured vertical distance. The variable rate particulate application device outputs a particulate application rate and the control system varies the particulate application rate.

In still another aspect, the present invention relates to a mobile turf measurement apparatus for measuring a synthetic turf infill profile, which comprises a frame, at least one probe, a plate, a sensor and a computer. The frame is adapted for substantially hand-held operation. The at least one probe is configured to locate a lower position of the profile. The plate is configured to locate an upper position of the profile. The sensor is positioned on the frame for measuring a vertical distance between the upper profile position and the lower profile position. The computer has a central processing unit, a memory coupled to the central processing unit and an electronic interface coupled between the instrument and the memory for transferring the measured vertical distance.

In still another aspect, the present invention relates to a method for sensing a synthetic turf infill profile comprising the steps of sensing the infill profile, determining a particulate application rate and applying particulate. The method includes selecting a desired vertical height of the infill profile into an input device. The method further includes sensing a lower position of the profile at a location and sensing an upper position of the profile at the location. The method further includes determining a particulate application rate and applying a quantity of particulate correlating to the application rate to the location.

BRIEF DESCRIPTION OF THE DRAWINGS

This invention will be described hereafter in the Detailed Description, taken in conjunction with the following drawings, in which like reference numerals refer to like elements or parts throughout.

DETAILED DESCRIPTION

Figure 1:
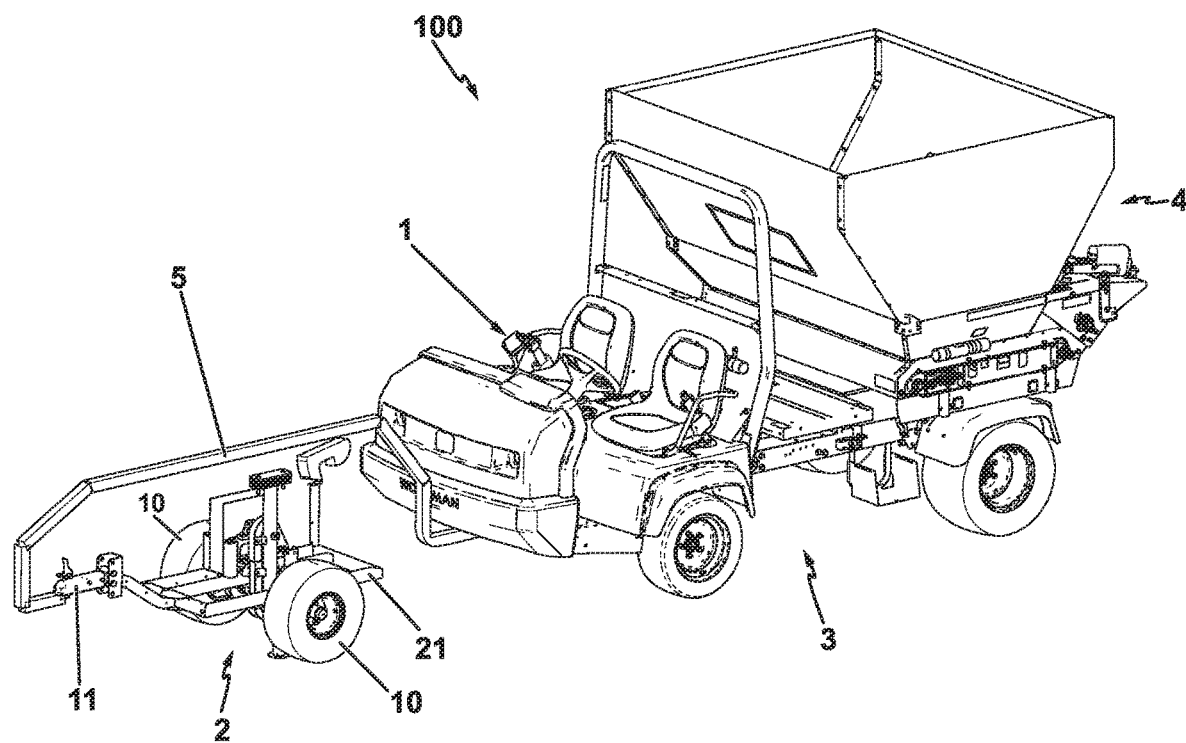
FIG. 1 is an overhead perspective view towards the front of one embodiment of a mobile turf measurement apparatus along with a motive device, input device and variable rate top-dressing device according to this invention.

FIG. 1 illustrates one embodiment of a mobile turf instrument apparatus 100 including a measurement apparatus 2, an input device 1, a motive device 3, and a top-dressing device 4, according to this invention. Top-dressing device 4 is preferably mounted on the rear of motive device 3. Measurement apparatus 2 comprises a frame 21 supported for rolling over the ground by one or more rotatable ground engaging members, such as by a pair of wheels 10. Frame 21 carries a hitch 11 to releasably couple measurement device 2 to the front end of a forwardly extending tow arm 5 that is carried on motive device 3, such as a utility vehicle as depicted in FIG. 1, a mower (not shown), or the like. This allows motive device 3 to propel measurement apparatus 2 over the ground as motive device 3 is self-propelled over the ground by an onboard prime mover (not shown) chive train (not shown) both carried on motive device 3.

Alternatively, measurement apparatus 2 could be pushed by motive device 3 rather than being towed. Moreover, measurement apparatus 2 could itself be self-propelled with an onboard prime mover (not shown) and drive train (not shown) carried on frame 21. In addition, frame 21 could be remotely controlled or operate independently through sensor-assisted navigation. Frame 21 preferably includes sufficient weight to minimize vertical movement of frame 21 as it is moved over the ground. Alternatively, weight could be added to frame 21 to minimize vertical movement of frame 21 as it is moved over the ground.

Measurement apparatus 2 has many similarities to that disclosed in U.S. Pat. No. 7,628,059, which is owned by The Toro Company, the assignee of this invention. The basic revolving arm motion that is used to carry a probe assembly into and out of contact with the ground is substantially the same in measurement apparatus 2 of this invention to that disclosed in the '059 patent. Accordingly, the '059 patent is hereby incorporated by reference for teaching the details of the revolving arm and how it is used to carry a probe assembly, albeit a probe assembly which is different in this invention from the probe assembly disclosed in the '059 patent, into and out of the ground.

Figure 2:
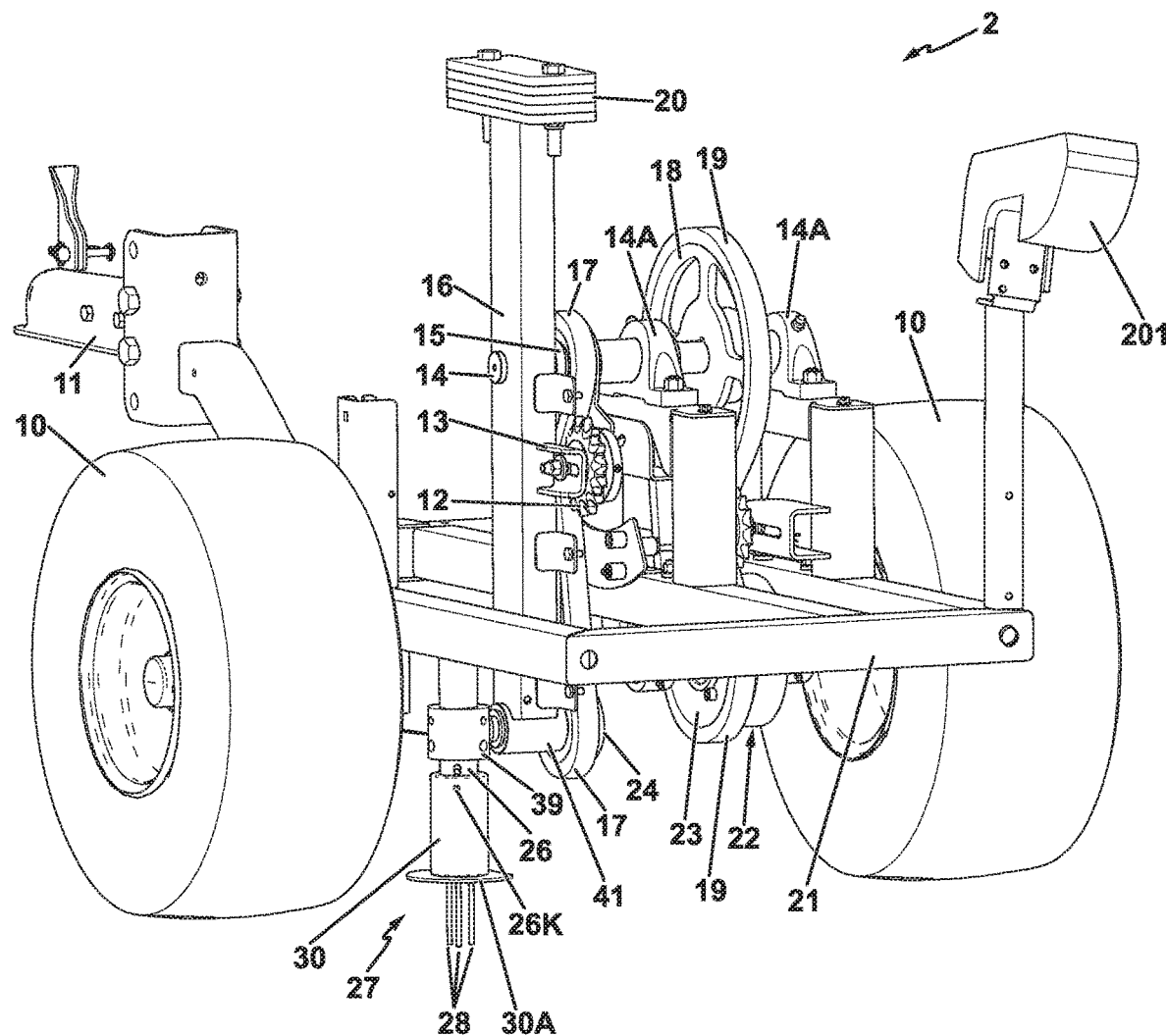
FIG. 2 is a perspective view towards the rear of the mobile turf measurement apparatus of FIG. 1.

By way of an overview of the common revolving arm used in both the '059 patent and in measurement apparatus 2 of this invention, apparatus 2 includes an elongated revolving arm 16 which is fixed to a substantially horizontal shaft 14 so as to rotate with shaft 14. Shaft 14 is rotatably journal led on frame 21 by a pair of spaced bearings 14A carried on frame 21, See FIGS. 2 and 3.

Arm 16 is revolved by a drive taken from the stub axle 22A of one wheel 10 of frame 21. A first small drive sprocket 23 non-rotatably carried on stub axle 22A and a second larger driven sprocket 18 non-rotatably carried on shaft 14 are connected together by a chain 19 to provide a speed reduction between the rotational speed of wheels 10 and that of arm 16. A clutch 22, either electric or mechanical, is also carried on stub axle 22A to selectively drive stub axle sprocket 23. In other words, stub axle sprocket 23 is coupled to stub axle 22A and is rotated by stub axle 22A when clutch 22 is engaged and conversely is uncoupled from stub axle 22A and is not rotated by stub axle 22A when clutch 22 is disengaged. As described more completely in the '059 patent which has been incorporated by reference herein, the engagement and disengagement of clutch 22 can be controlled by limit switches (not shown herein) that are carried on frame 21 and are engaged by a magnet or other trigger carried on arm 16, the triggering of a first limit switch causing clutch 22 to become disengaged and the triggering of a second limit switch causing clutch 22 to become reengaged. The period in which clutch 22 is disengaged may correspond to the time at which a turf measurement is being taken by measurement apparatus 2.

A probe assembly 27 is rotatably mounted on one end of revolving arm 16 by a mount 39 comprising a mounting collar 39B having a horizontally outwardly extending pivot shaft 39A affixed thereto. Pivot shaft 39A extends through a bearing 40 in a hub 41 on the end of arm 16. Pivot shaft 39A is non-rotatably keyed or splined to a small sprocket 24 that is also carried on the end of arm 16. See FIG. 5. Rotation of probe assembly sprocket 24 relative to the end of arm 16 will also rotate probe assembly 27 relative to the end of arm 16.

Probe assembly sprocket 24 on the end of arm 16 is coupled by a chain 17 to a fixed sprocket 15 that is carried concentrically around horizontal shaft 14 that rotates arm 16. While fixed sprocket 15 is concentrically positioned around shaft 14 to be on the same axis as shaft 14, fixed sprocket 15 is not rotatably coupled to shaft 14 and is not part of arm 16. Fixed sprocket 15 is so named because no rotation of sprocket 15 is allowed relative to frame 21. Instead, fixed sprocket 15 is physically clamped or held relative to frame 21 so that it does not rotate. A rotatable idler sprocket 12 is mounted by a bracket 13 on arm 16 substantially immediately beneath fixed sprocket 15. See FIG. 2. Idler sprocket 12 helps maintain proper tension on chain 17 during rotation of arm 16.

As arm 16 rotates around horizontal shaft 14 in a given direction, chain 17 produces an equal and opposite counter-rotation of probe assembly sprocket 24 so that foot 30 and its ground engaging plate 30A (see FIG. 4A), located at or near the lower end of probe assembly 27, always remain substantially horizontal relative to frame 21 and relative to the ground during rotation of arm 16. Thus, probe assembly 27 is self-leveling relative to arm 16 as arm 16 rotates or revolves with shaft 14 around the axis of shaft 14.

Figure 4A:
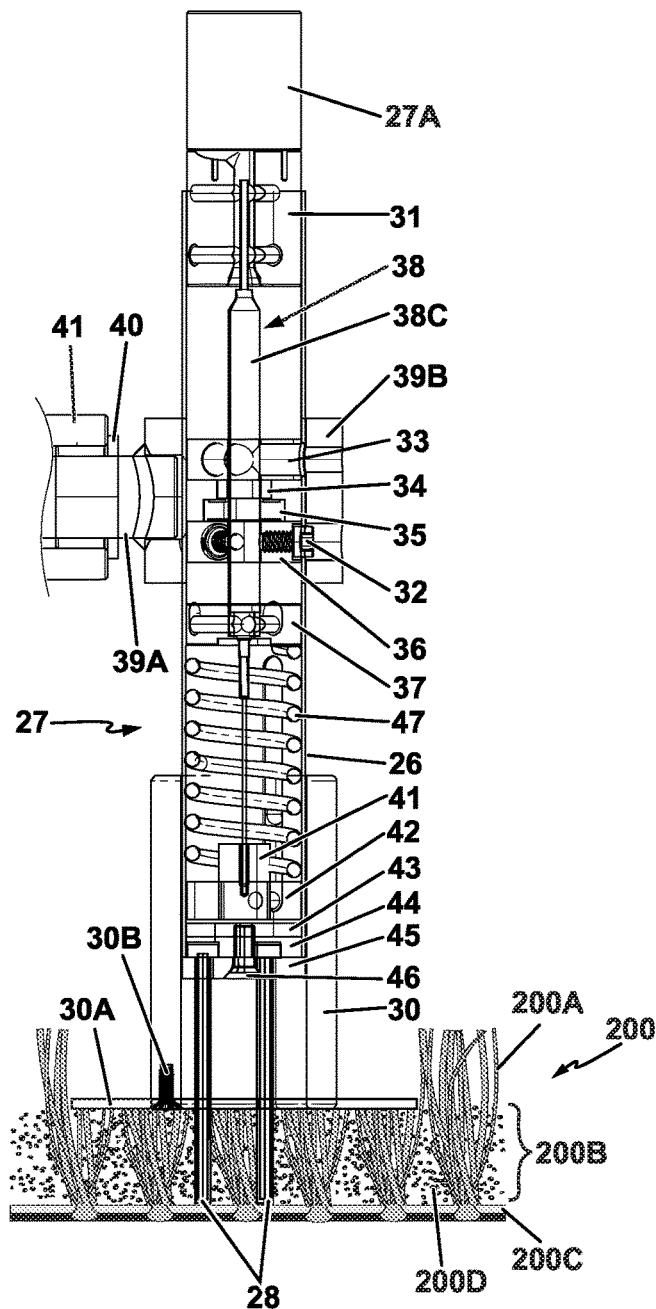
FIG. 4A is a side-elevation cross-sectional view of the probe assembly of the mobile turf instrument apparatus of FIGS. 2 & 3.
Figure 4B:
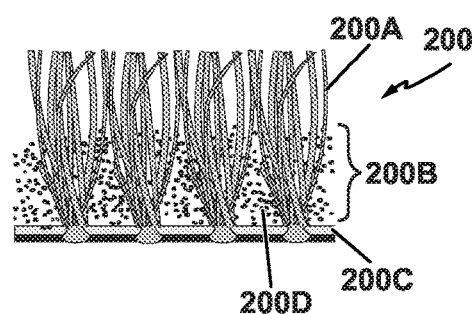
FIG. 4B is a side-elevation cross-sectional view of a synthetic turf composition.
Figure 5:
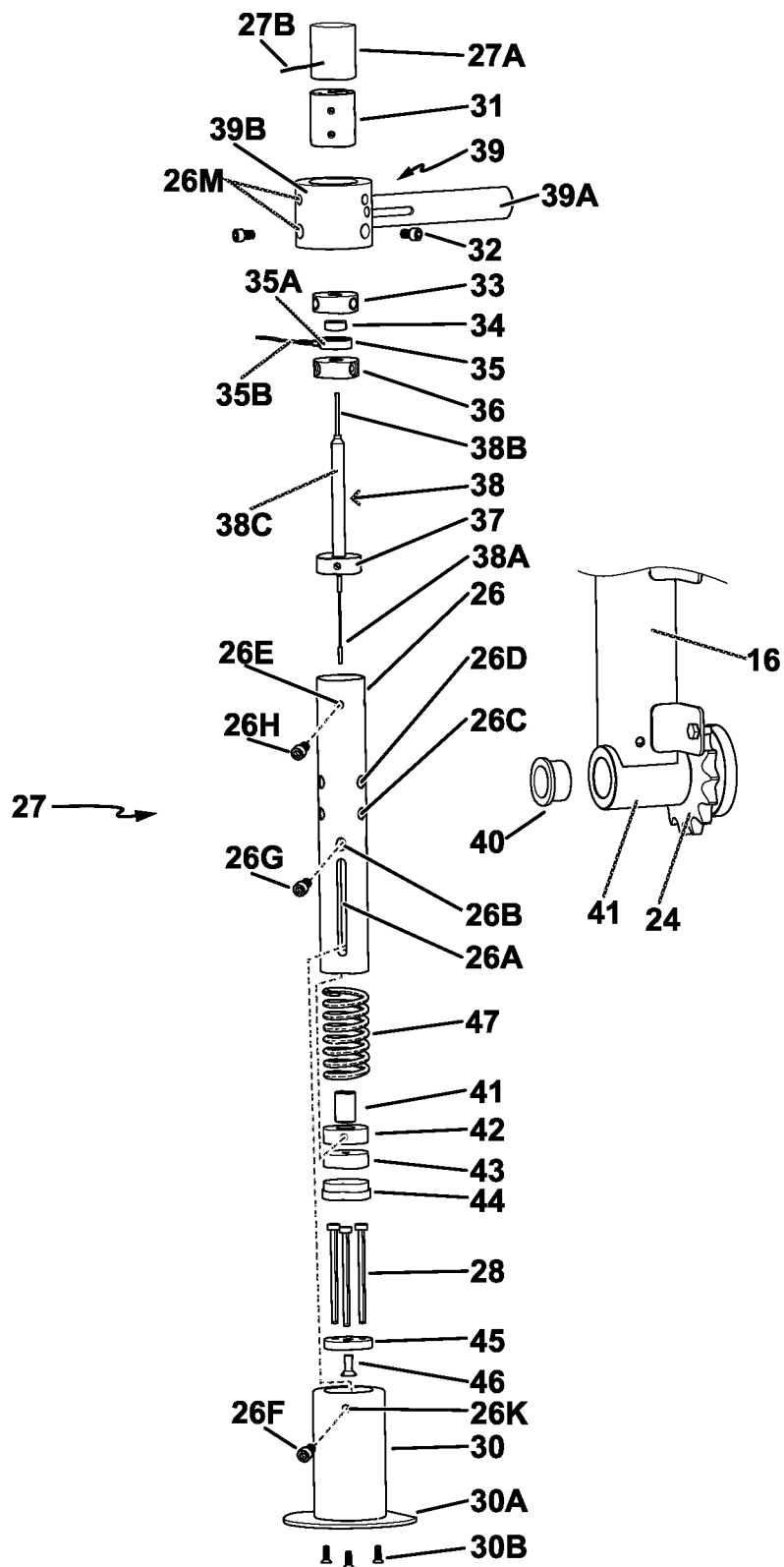
FIG. 5 is an exploded perspective view of the probe assembly of FIG. 4.

FIGS. 4A & 5 depict one embodiment of probe assembly 27. FIG. 4A depicts probe assembly 27 engaged in a synthetic turf profile 200B. FIG. 4B depicts a typical synthetic turf profile which will be referenced throughout this application and in relation to other embodiments. Synthetic turf profiles may vary between compositions but generally include, turf fibers 200A, infill particulate 200D) and fiber backing 200C. The vertical height of infill particulate 200D is indicated by infill particulate profile 200B.

Turf instrument apparatus 100 is designed to sample particulate profile 200B at various spaced locations over a turf surface to determine the height of the particulate profile 200B over the entire turf surface, namely to determine the variation of the height of the particulate profile 200B relative to a nominal or desired height over the entire turf surface. In addition, apparatus 100 can then potentially take appropriate corrective action to add particulate infill to any sampled locations that have been determined to be below the nominal or desired height. If any sampled locations have been determined to be above the nominal or desired height, apparatus 100 will not add any particulate infill to such sampled areas.

Turning now to a fuller description of probe assembly 27, in addition to mount 39, probe assembly 26 also includes a substantially cylindrical, hollow probe body 26 and a hollow, cylindrical foot 30. Cylindrical foot 30 has an open lower end that is largely closed by an enlarged bottom horizontal plate 30A that is secured to foot 30 by fasteners 30B to form a single unit. See FIG. 4A. The upper end of foot 30 is open and is slidably received around the lower end of probe body 26. Thus, foot 30 and its conjoined bottom plate 30A are vertically movable upwardly and downwardly relative to probe body 26 as will be detailed hereafter.

Figure 3:
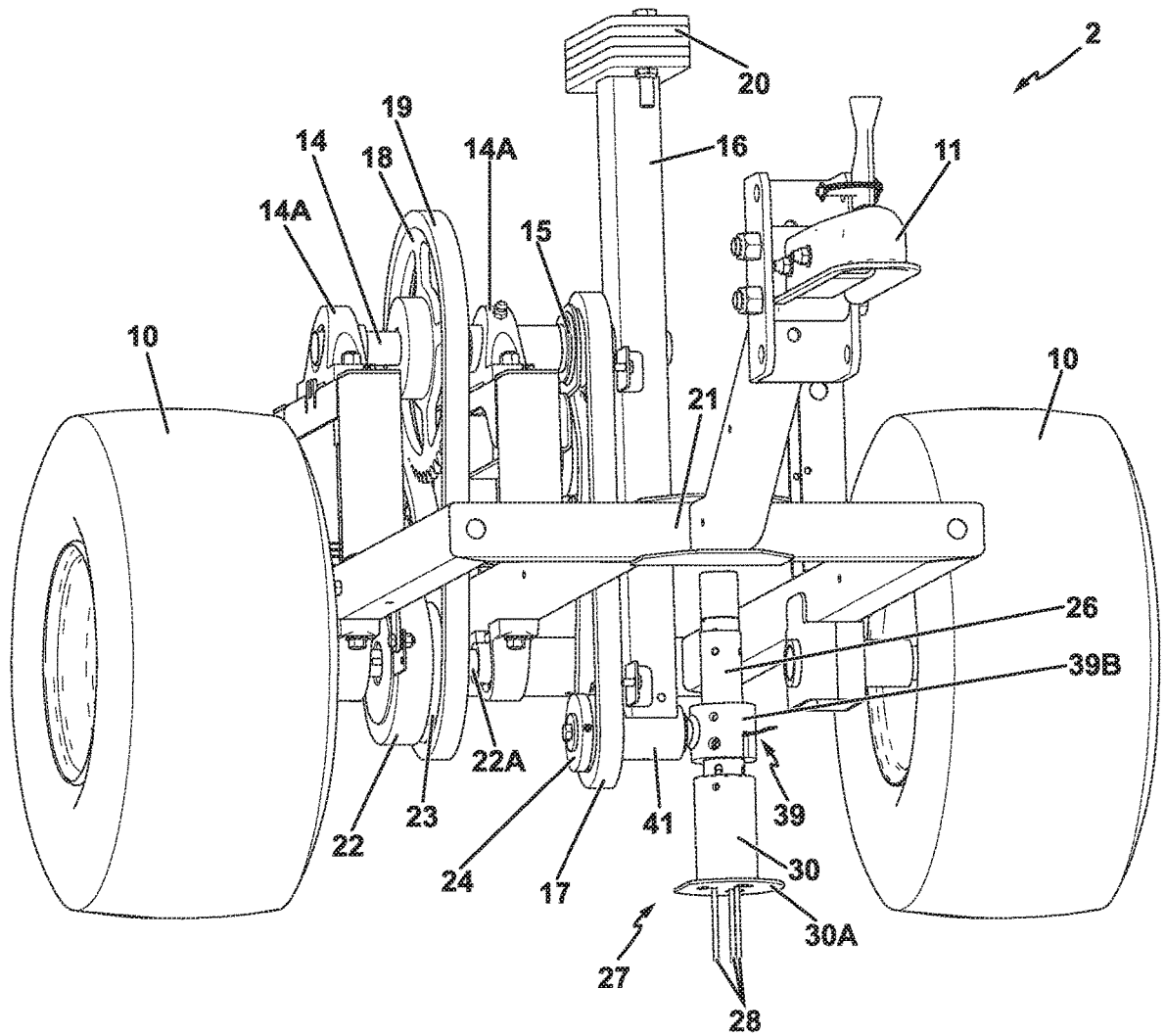
FIG. 3 is a perspective view towards the front of the mobile turf instrument apparatus of FIG. 1.

Bottom plate 30A of foot 30 has three apertures through which three cylindrical probes 28 may extend as illustrated in FIG. 3. Normally when measurement apparatus 2 is not sampling the height of the particulate profile 200B, foot 30 will be lowered on probe body 26 until the tips of probes 28 are retracted up, relative to foot 30, into the plane of bottom plate 30A. However, when so retracted, it is preferred that probes 28 do not disengage the apertures in the plane of bottom plate 30A so as to always have guiding support therefrom.

The aforementioned three cylindrical probes 28 are fixedly secured to the bottom of probe body 26 in a substantially vertical position in relation to the ground by a lowermost probe retaining plate 45, a probe stop 44 and a threaded probe fastener 46. Probe fastener 46 extends upwardly through a central aperture in probe retaining plate 45 to be tightened into a threaded aperture in probe stop 44. Probe stop 44 is fixedly secured within the lower end of probe body 26 to have a fixed, non-movable vertical and horizontal position within probe body 26. When probe fastener 46 is tightened, the enlarged upper heads of probes 28 will be retained in downwardly opening pockets in the underside of probe stop 44 by the clamping force provided by the underlying probe retaining plate 45 and probe fastener 46. Probes 28 will extend downwardly through various apertures in probe retaining plate 45 and through the corresponding apertures provided therefor in bottom plate 30A of foot 30, thus effectively supporting probes 28 at both their upper and lower ends. Although three probes 28 are preferable to establish a plane representative of backing 200C, any number of probes 28 can be used and shapes other than cylinders may be used, such as a cone, pyramid or cuboid.

Within the lower portion of probe body 26, a spacer 43 is positioned immediately above probe stop 44 though spacer 43 may be integrated into probe stop 44 if so desired. Spacer 43 helps align the various portions of the vertically slidable connection between foot 30 and probe body 26. In this regard, a pair of circumferentially spaced apertures 26K in the upper end of foot 30 receive a pair of threaded fasteners 26F. Fasteners 26F pass through apertures 26K in foot 30, through two vertically extending slots 26A on opposite sides of probe body 26, and finally into circumferentially spaced threaded holes on opposite sides of a lower sensor base 42.

The dotted lines in FIG. 5 indicate the path of one of the fasteners 26 as it passes through aperture 26K in foot 30, through slot 26A, and finally into lower sensor base 42, keeping in mind that the parts are shown in exploded form in FIG. 5. In reality, each fastener 26 would extend directly horizontally through one aperture 26K in foot 30, through the adjacent slot 26 A in probe body 26, and into one aperture in lower sensor base 42 when probe assembly 27 is in an assembled form. A lower sensor receiver 41 is fixed to lower sensor base 42.

A vertically elongated sensor 38, e.g. a linear potentiometer, has a sensor body 38C with a movable sensor shaft 38A that protrudes downwardly from body 38C. The lower end of sensor shaft 38 A is fixed to lower sensor receiver 41. Thus, fasteners 26F secure together, as a single integrated group, foot 30, lower sensor base 42, lower sensor receiver 41, and sensor shaft 38A, to permit vertical movement of this group of components along slots 26A in probe body 26 while substantially restricting horizontal and rotational movement of this group of components in relation to probe body 26. When such vertical movement occurs because of foot 30 engaging the particulate profile 200B in the turf, the upward movement of foot 30 along the lower end of probe body 26 will carry with it the vertically movable sensor shaft 38A causing such sensor shaft 38A to be retracted within sensor body 38C. The degree of the retraction of sensor shaft 38 A within sensor body 38C is then sensed and recorded as an indication of the height of the particulate profile 200B relative to the backing material 200C.

Sensor body 38C is itself fixed within probe body 26 by fasteners 26G. Fasteners 26G pass through holes 26B in probe body 26 and threadably engage and extend through an upper sensor receiver 37 to engage sensor body 38C. Fasteners 26G, along with holes 26B, restrict substantially all vertical, horizontal or rotational movement of upper sensor receiver 37 and sensor body 38C in relation to probe body 26.

A coil spring 47 is positioned within probe body 26. The upper end of spring 47 abuts the bottom surface of upper sensor receiver 37 and the lower end of spring 47 abuts the top surface of lower sensor base 42. Spring 47 collectively biases as a group, foot 30, fasteners 26F, lower sensor base 42, lower sensor receiver 41, and sensor shaft 38A toward the lower end of probe body 26. As noted earlier herein, when plate 30A is not in contact with a turf surface, spring 47 forces fasteners 26F to slide to the bottom of slot 26A, concurrently placing foot 30 and its bottom plate 30A at its lowermost position on probe body 26. In this position, it is desirable that the bottom surface of plate 30A be substantially coplanar with the tips of probes 28. Thus, probes 28 are protected by bottom plate 30A when not engaged with a surface but still have guiding support by the apertures in bottom plate 30A and the overall height of probe assembly 27 is minimized. Alternatively, the bottom surface of plate 30A need not be substantially coplanar with the tips of probes 28 with such tips extending at least somewhat below bottom plate 30A even in the lowermost position of foot 30.

Mount 39 pivotally couples probe body 26 to arm 16. Fasteners 32 pass through holes 26M in mounting collar 39B, through holes 26C, 26D in probe body 26, and into holes in an upper mounting spacer 33 and a lower mounting spacer 36. A load cell 35 comprises a load cell body 35A and electrical wire 35B. Load cell body 35A is positioned within probe body 26 above lower mounting spacer 36 and below a load cell spacer 34 which is itself positioned below upper mounting spacer 33. Upper mounting spacer 33, load cell spacer 34, load cell 35 and lower mounting spacer 36 all possess an opening at their axial center, in which sensor body 38C is disposed without being directly supported thereby.

Holes 26C, 26D in probe body 26 are slightly vertically elongated to provide a small amount of vertical movement of probe body 26 in relation to mounting collar 39B when probes 28 are acted upon by turf backing 200C. This enables a measurement of vertical force by load cell 35 which is useful in determining whether probes 28 have passed through the entire infill profile 200B and reached backing 200C. On the other hand, holes 26B through which fasteners 26G extend are vertically elongated equal to or greater than the elongation of holes 26C, 26D to prevent the transference of force acting upon probes 28 to senor 38 thereby minimizing vertical movement of sensor 38 in relation to probe body 26 to maximize the precision of measurement apparatus 2.

Finally, fasteners 26H pass through holes 26E in probe body 26 and engage a cap 31, thereby securing cap 31 to probe body 26. A vibratory device 27A is secured to upper surface of cap 31, providing vibratory movement to probe body 26 and thus to probes 28. Other examples may not include a vibratory device 27A.

It is preferable when using three cylindrical probes 28 that the diameter of the probes range from 0.1 to 0.2 inches to provide probes 28 with sufficient strength to prevent buckling while preventing penetration through backing 200C. However, other diameters may be used as long as the equivalent diameter is not greater than the horizontal spacing of fibers 200A at backing 200C to permit probes 28 to reach backing 200C. Equivalent diameter refers to the greatest distance between two points in any horizontal cross-section of a probe 28, when the horizontal cross-section is anything other than a circle. It is also preferable that probes 28 have diameters that are less than the horizontal spacing of fibers 200A at backing 200C, to reduce the pressure required to move probes 28 downward through profile 200B.

It is preferred that pressure applied by probes 28 to the infill profile 200B be somewhere in the range between 700 and 4000 pounds per square inch (PSI) so that probes 28 actually reach backing 200C. However, other pressures may be applied depending on the composition of the synthetic turf profile. Weight may be added to frame 21 in order to increase the pressure applied by probes 28. Furthermore, the actuation of vibratory device 27 may reduce the pressure required to reach backing 200C. lit is preferable that the lower surface area of plate 30A of foot 30 be from 1 to 30 square inches to obtain a sufficient contact area with the infill profile surface. In addition, it is preferable that the pressure applied to the lower surface of plate 30A be from 0.5 PSI to 8 PSI to obtain repeatable and accurate vertical distance measurements. However, other pressures may be applied depending on the composition of the synthetic turf profile.

It should be clear that both load cell 35, sensor 38, and vibratory device 27 A are electrically connected to various controls and measurements located elsewhere. These electrical connections are diagrammatically illustrated by electrical wires 35B, 38B, and 27B. Thus, the readings that are derived from load cell 35 and sensor 38 can be logged or recorded in any appropriate device, such as a data logger or computer. The computer may be carried on frame 21 itself, or on the motive device 3 used to propel the frame 21 (e.g. within input device 1 on motive device 3), and may be hardwired to load cell 35, sensor 38 and vibratory device 27A as suggested by wires 35B, 38B, 27B. Alternatively, wireless communication could be established between load cell 35, sensor 38, and vibratory device 27A to allow the readings to be wirelessly communicated to input device 1, a computer or a data logger.

As frame 21 moves across the turf and when clutch 22 is engaged, arm 16 will rotate or revolve from the drive taken from wheel 10. As arm 16 revolves, probe assembly 27 rotates correspondingly in a way that maintains probe assembly 27 in a vertical position with probes 28 facing the ground. At some point, arm 16 will approach the ground and probes 28 will be pushed into the synthetic turf profile 200.

Clutch 22 can be disengaged to uncouple arm 16 from the drive from wheel 10 from some time shortly before probes 28 have entered the ground (assuming arm 16 has sufficient momentum) to some time shortly after probes 28 have entered the turf profile 200B. If clutch 22 is disengaged shortly before probes 28 have entered the turf profile 200B and the speed of the arm is high enough, then the momentum of arm 16 will be sufficient to cause arm 16 to continue to rotate and to insert probes 28 in the turf profile 200B. Once probes 28 are inserted into the turf profile 200B, then arm 16 will continue to rotate since probes 28 are now stuck in the turf profile 200B but frame 21 is continuing its forward motion. Thus, when the drive is actually disconnected from arm 16 from a moment just prior to or just after probe insertion and/or during the entire time probes 28 are in the turf profile 200B, arm 16 will to the naked eye look like it is revolving as before.

During the time the drive is disconnected from arm 16, vibratory device 27A may be activated, thereby vibrating probe body 26 during the insertion of probes 28 into turf profile 200B. Particulate 200D is often comprised of rubber particulate and another particulate having a density greater than rubber such as sand. Often a sand particulate, through turf use, brushing or irrigation, will settle over time towards the lower portion of turf profile 200B. This increased concentration of sand particulate to rubber particulate in the lower portion of profile 200B can impede the downward motion of probes 28 and may provide a false measurement of the infill height of profile 200B. Vibratory device 27A may assist the movement of probes 28 through profile 200B and thereby reduce the required downward pressure on probes 28 to reach backing 200C. This reduces the risk of puncturing backing 200C.

There are two reasons for disconnecting the drive to arm 16 while probes 28 are inserted into the turf profile 200B. One is to avoid having probes 28 make elongated holes or slots in the turf profile 200B. The other is to avoid putting too much torque or stress on probes 28 or on the other components of probe assembly 27 while probes 28 are in the turf profile 200B. This will further help avoid damaging probes 28 or the other components of probe assembly 27.

In any event, the drive disconnection to arm 16 lasts only so long as probes 28 are in the ground. When arm 16 swings around past bottom dead center and probe assembly 27 is about to begin, or has recently lifted, probes 28 out of the turf profile 200B, clutch 22 is reengaged. This couples arm 16 to the drive from wheel 10 to continue the rotation of arm 16 again through another cycle of operation.

When probes 28 are in the turf profile 200B, the computer samples the electrical output of sensor 38, converting that electrical value to a distance between the tips of probes 28 (lower profile position) and the surface of plate 30A (upper profile position). This distance is, in effect, a measurement of the vertical height of the infill particulate 200D above the backing 200C. Sensor 38 is preferably a linear potentiometer. However, another type of sensor can be used in substitution of or in combination with sensor 38, including membrane potentiometers, draw wire transducers and Hall effect sensors.

During the same sampling intervals of sensor 38, the computer can also sample the electrical output of load cell 35, converting the electrical output to a force. The computer then selects the largest distance value sampled representing the largest vertical height of the infill particulate at the sampled spot of the infill profile 200B. Alternatively, the computer could select: the minimum distance value, the value at a specific time during surface engagement, the value at a geographic location, a series of values or a statistical computation of a series of values captured by sensor 38. The computer could also select the force, as measured by load cell 35, recorded at the time that any of the above-identified distance values were captured to correlate the load cell readings with the distance value readings. These vertical distance values derived from sensor 38 and the correlating load force readings from load cell 35 will be recorded in the computer.

A GNSS device or other geographic locating device can be carried on frame 21 to assign a location to each vertical distance value and load force readings. Alternatively, vertical distance and force measurements can be assigned a geographic location if a predetermined path is programmed into the computer and that same path is followed by the frame 21. Moreover, a measurement can be assigned a geographic location through monitoring the rotation of the trailer wheels 10 (e.g. independent odometers). The computer can repetitively record independent wheel odometer data and record when vertical distance and force measurements were recorded to recreate a geographic path and assign each vertical distance and force measurement to a location along the geographic path. Thus, the reported vertical distance and force measurements can be correlated to the location where the reading was taken.

Furthermore, the reported vertical distance and force measurement can be compiled and displayed in a geographic map representation of profile 200B measurements. In addition, the recorded distance can be analyzed by the computer and the computer can send, nearly instantaneously, data to a top-dressing device 4 (see FIGS. 1 & 7) which can substantially immediately apply an amount of top dressing required to bring measured any low spots in infill profile 200B up to a desired or nominal vertical distance (height) while not adding any top dressing to any high spots in infill profile 200B. Alternatively, top-dressing device 4 need not be conjoined with measurement apparatus 2 or work at the same time as measurement apparatus 2. Measurement apparatus 2 could work independently of top-dressing device 4 and store a map of the infill profile 200B for a particular area of turf. At some later time, a top-dressing device 4 could then be driven back over the same area of turf and be operated to fill in the low spots in the previously stored map of the turf area using GPS positioning of the top-dressing device to coordinate the application of the particulate 200D in accordance with the map coordinates.

Figure 6:
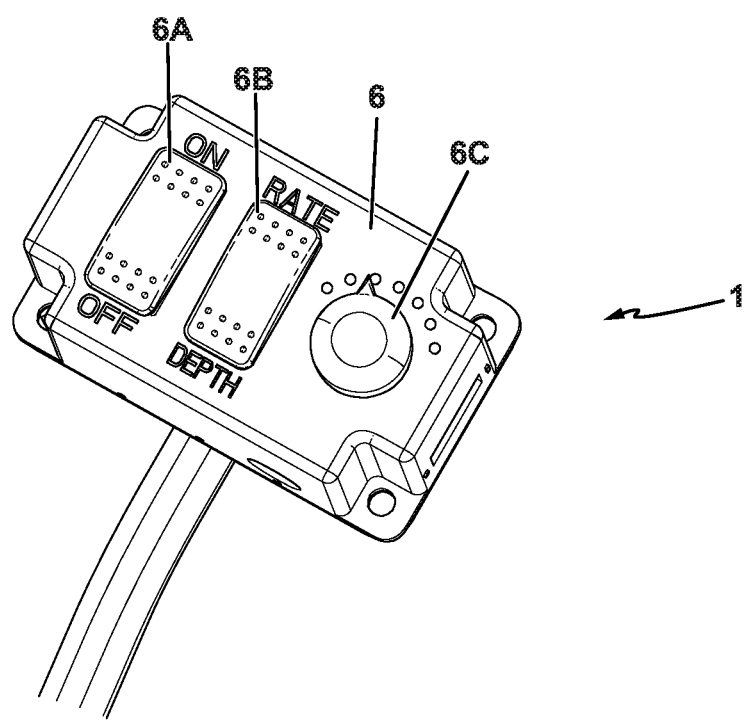
FIG. 6 is a perspective view of the input device of FIG. 1.

Now referring to FIG. 6, input device 1 has a housing 6 in which a computer is located. Alternatively, a computer may be positioned in a variety of locations, on frame 21, within input device 1, on motive device 3, or on top-dressing device 4. Input device 1 allows an operator to set both a desired rate of application and a desired vertical height of infill particulate profile 200B. Input device 1 controls the measuring process and correlates particulate application by rocking the switch 6A to the "on" and then to the "off" position to initialize the computer. Next, the desired rate is set by rocking switch 6B to the "rate" position and then adjusting dial 6C to the desired application rate. The desired rate is the maximum rate of infill application. This selection limits the amount of infill particulate that may be applied at a given time. For example, the computer would adjust the quantity of the infill particulate application rate if the determined application rate exceeds the desired rate. Dial 6C has markings that correlate to both application rates and vertical height of particulate profile. The desired vertical height of profile 200B is set by rocking switch 6B to the "depth" position and adjusting dial 6C to the desired vertical height of profile 200B.

Next the operator moves apparatus 100, through control of the motive device 3, towards the desired measurement location. As the motive device reaches a consistent velocity, and approaching the desired measurement location, the operator, actuates switch GA to the "on" position, which initiates the engagement of clutch 22. The preferable velocity is approximately two miles per hour, but other velocities may be selected. Apparatus 2 then functions as follows. Clutch 22 is disengaged as probe assembly 27 approaches the ground. Foot 30 contacts the top of the turf profile with probes 28 becoming extended out through the bottom plate 30A of foot 30 such that probes 28 push down through the turf profile to reach backing 200C. During this probe insertion phase, measurements of the distance the bottom plate 30A of foot 30 has risen above the tips of probes 38 as indicated by the vertically upward motion of sensor shaft 38A into sensor body 38C caused by the motion of foot 30 are sent to the computer and, recorded in input device 1. These infill height measurements are collectively analyzed by the computer in relation to operator-selected application rate and the desired vertical profile height to determine an application rate, to output a correlating application signal to top-dressing device 4, and to substantially simultaneously apply the top-dressing material to any low spots in a one pass operation of the type that can be conducted by apparatus 100 of FIG. 1. As the foot 30 lifts up off the turf profile and lowers back down over probes 28 which are retracted up out of the turf profile, clutch 22 will be reengaged to drive arm 16 around for another cycle of operation.

Moving in a straight line at a speed of two miles per hour, apparatus 2 will measure profile 200B approximately every eight feet. The process of measuring particulate profile 200B, recording such measurements in input device 1, processing that measurement by a computer in relation to operator-selected rate application and vertical profile height, outputting a signal to top-dressing device 4 and top-dressing device 4 applying an amount of infill particulate correlating to the output signal may be repeated for each independent particulate profile 200B measurement. With a sample interval of eight feet, the computer applies the same application rate of top-dressing to the four feet prior to the measurement and the adjacent four feet after the measurement. Therefore, an area with a dimensional length of eight feet and a width equivalent to the application width of top-dressing device 4 receives a substantially uniform application of top-dressing. Alternatively, a different sampling interval could be utilized, through modification to the drive system to arm 16, to alter the length dimension of the uniform application area.

Alternatively, a computer may interpolate measurements and send an output signal or a series of output signals to top-dressing device 4 to apply particulate in varying amounts between two consecutive measurements. Moreover, input device 1 may be mounted anywhere on apparatus 100 or exist in a remote configuration with wireless connectivity to measurement apparatus 2 and top-dressing device 4. For example, input device 1 may exist on a portable electronic device with wireless connectivity, such as a smart phone or tablet computer in a manner in which the parameters controlled by physical switches 6A, 6B and dial 6C are controlled in a user interface. Rocking switch 6A to the "off" position disengages clutch 22 and sends a signal to the computer, which is processed by the computer, and the computer starts a timer, based on the assumed velocity of two miles per hour, and sends an output signal to terminate particulate application after the timer has expired. Alternatively, the actuation of switch 6A could be controlled with a geographic locating system which senses when apparatus 2 has entered a desired sampling area and virtually actuates switch 6A to the "on" position, initiating the sampling process, and senses when apparatus 2 has exited the same sampling area, virtually actuating switch 6A to the "off" position, deactivating the sampling process.

Figure 7:
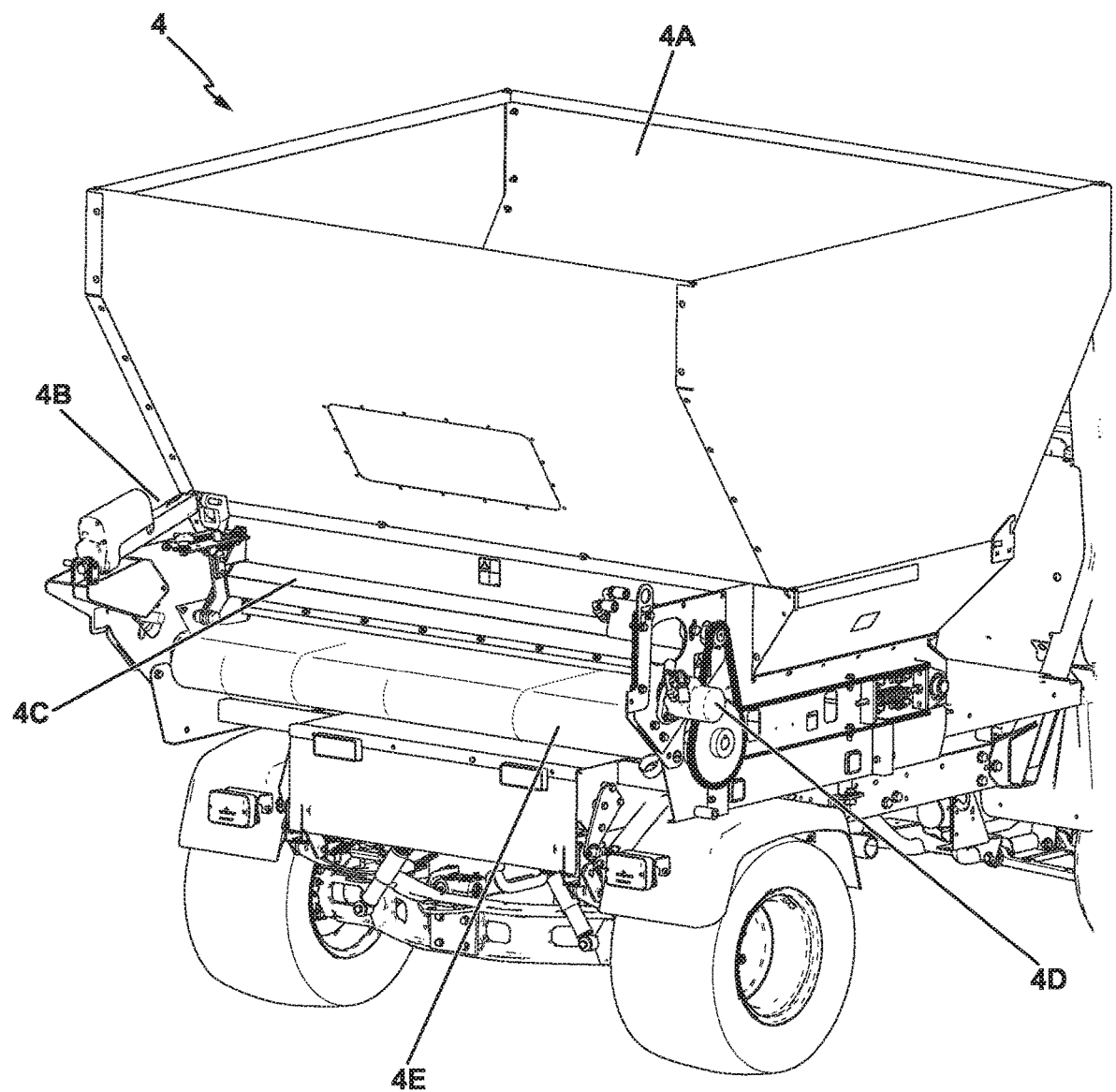
FIG. 7 is a perspective view towards the rear of the top-dressing device of FIG. 1.

FIG. 7 depicts top-dressing device 4 along with top-dressing particulate storage hopper 4A, proportionally controlled hydraulic motor 4D, particulate dispensing belt 4E, actuator 4B and gate linkage 4C. During operation, the computer outputs a signal to both actuator 4B and motor 4D. The proportional control of motor 4D controls the velocity of belt 4E through a series of chains and sprockets. Alternatively, many other drive mechanisms may drive belt 4E, such as a direct-drive electrical motor. Actuator 4B actuates gate linkage 4C, thereby altering the area in which top-dressing particulate can pass through. Alternatively, devices other that actuators may be used to actuate linkage 4C, such as a rotating driver paired with a tracked gate. In changing the application rate of top-dressing device 4, the computer may be programmed to send a single signal to actuator 4B to articulate gate linkage 4C or send a signal to motor 4D to alter the velocity of belt 4E. Alternatively, the computer may be programmed to nearly simultaneously send dual signals, to both actuator 4B and motor 4D. Moreover, the computer may be programmed to switch between modes of single signal and dual signal adjustment. This switching mode may be preferred when a wide range of application rates are required, as a single adjustment of the motor or actuator may not be sufficient to output a desired application rate.

Similarly, the output of top-dressing device 4 can be recorded in ways similar to those described previously for the vertical distance measurement, compiled, and displayed in a geographic map.

In addition to measuring and recording parameters that are derived from the insertion of probes 28 into the profile, frame 4 could carry other turf instruments that do not depend upon such an insertion. For example, ground penetrating radar could be mounted at any suitable location on frame 21 to measure the distance between an upper and lower position within a profile, e.g. height of profile 200B.

Apparatus 2 of this invention provides for measuring various parameters of the turf using a probe assembly 27 that is periodically inserted into and removed from the turf profile 200B. It does so, however, by mounting such a probe assembly on a mobile frame 21 to allow the readings derived from probe assembly 27 to be accomplished automatically and without effort by the operator as frame 21 is driven or otherwise moved over the turf area to be surveyed and measured. This greatly enhances the productivity of the operator. The operator need not walk the turf area by foot and stick a hand-held soil moisture sensor into the ground. The vehicle need not be stopped to allow the probe assembly to be inserted into the ground.

In addition, frame 21 can be used to carry other turf measurement instruments, such as optical sensor 201, that measure other turf parameters using methods that do not require physical penetration of the turf profile 200B or in fact any engagement with the turf or the ground. Optical sensor 201 analyzes the visual appearance of the turf surface at a delayed interval according to the speed of apparatus 2, to analyze the exact area sampled by probes 28, calculating a ratio value of visible particulate 200D to visible fiber 200A. This ratio value would be sent to the computer and the computer would adjust the output signal to top-dressing device 4 if the ratio was greater than a programmed value. Thus, the application rate of top-dressing device 4 would be reduced if the ratio of particulate 200D to fiber 200A is greater that the programmed value. A ratio value above the programmed value indicates that the profile cannot or should not receive more particulate. It is possible that fiber 200A, when subjected to use, may break down or shorten in length. If the length of the fiber is below the desired or nominal profile height, as set on dial 6c, the area will have a higher ratio of particulate 200D to fiber 200A, and the ratio value of sensor 201 for that area would be greater than the programmed value, therefore the computer would reduce the application rate of top-dressing device 2. Thus, apparatus 2 of this invention can provide a whole range of turf parameter measurements and record and map such measurements over the turf area being surveyed. Obviously, sensors other than those described herein for measuring other turf parameters could be added to frame 21 of apparatus 2. For example, instruments for measuring reflectance or surface temperature could be added.

While a simple mechanical drive from wheel 10 is preferred for rotating arm 16, arm 16 could be driven by a separate hydraulic or electric motor. Thus, this invention is not limited to the specific details of the embodiment disclosed herein.

Figure 8A:
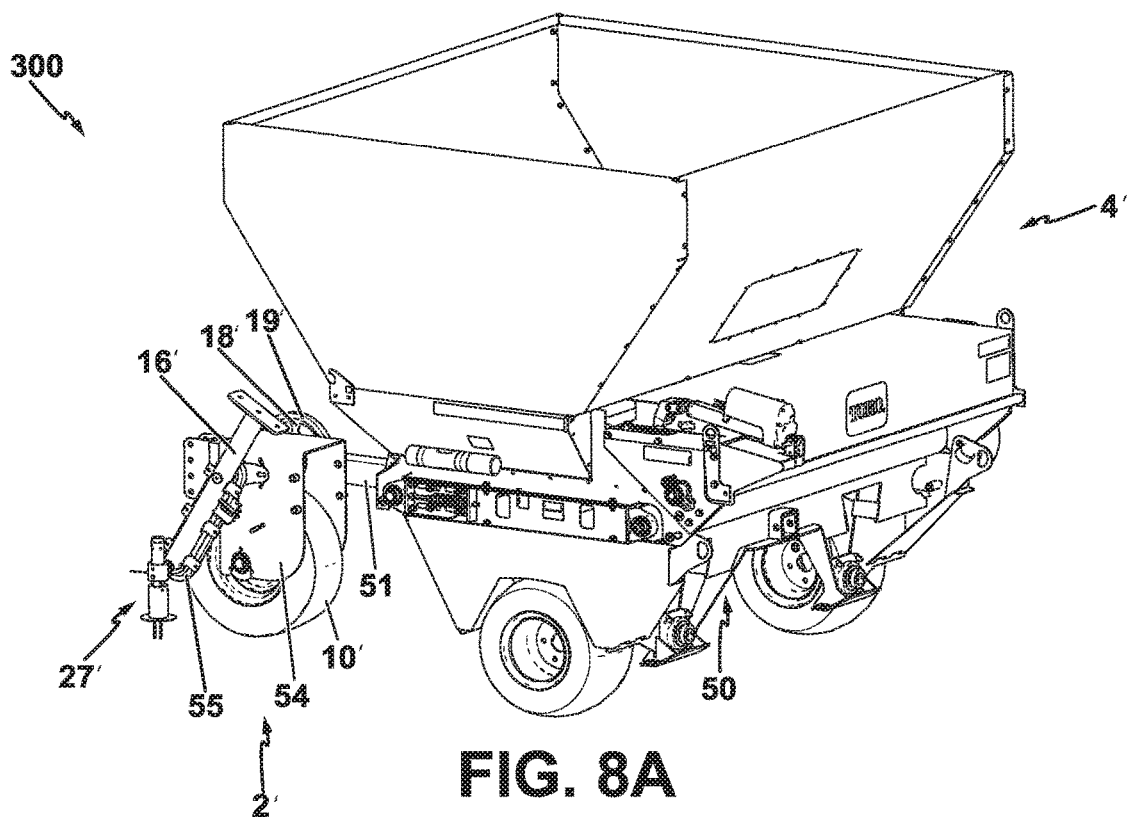
FIGS. 8A & 8B are perspective views of a second embodiment of a mobile turf measurement apparatus according to this invention mounted on a towable top-dressing device.
Figure 8B:
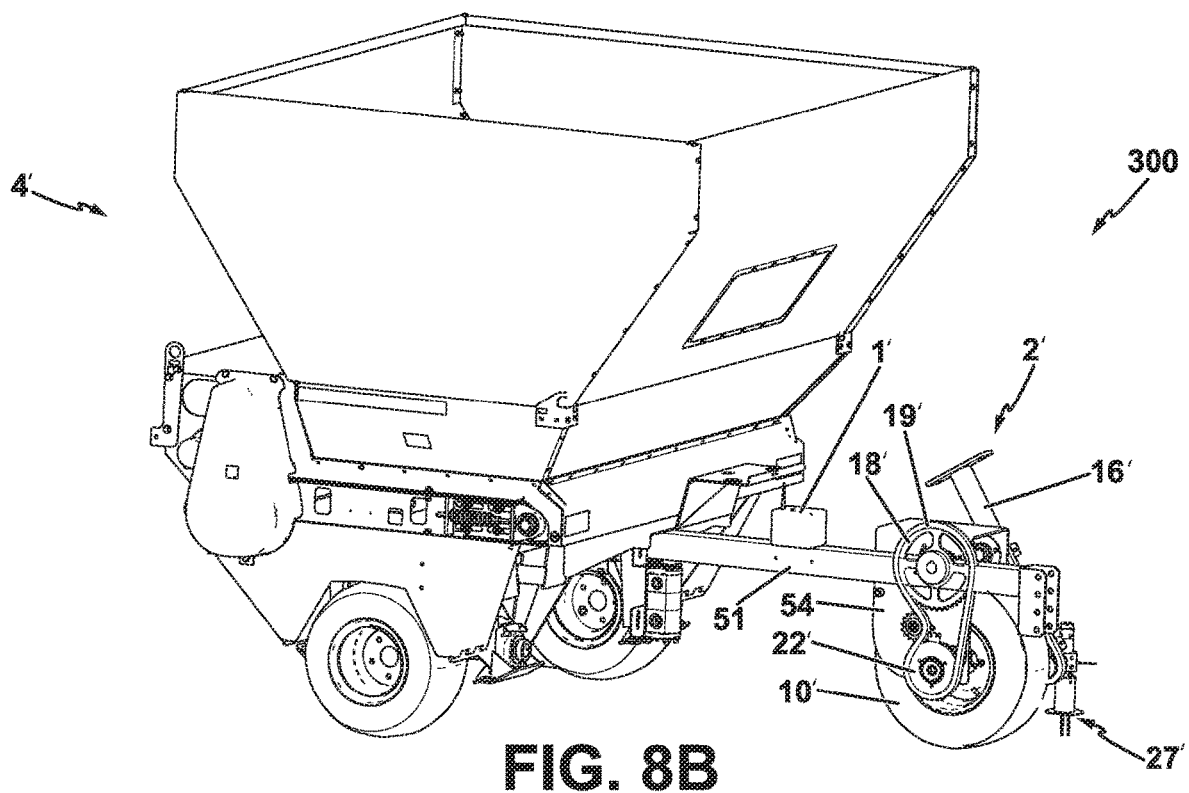

A second embodiment of a mobile turf instrument apparatus according to this invention is illustrated in FIGS. 8A & 8B as 300. Components of apparatus 300 that are the same as those of apparatus 100 will be referred to by the same reference numerals as used for those components of apparatus 100 but with a prime suffix being added, e.g. top-dressing device 4' versus top-dressing device 4. Much of apparatus 300 is the same as apparatus 100 including the use of a clutch 22' that drives a revolving arm 16' and input device. Thus, only the differences between apparatus 300 and apparatus 100 will be specifically described hereafter.

The major difference between apparatus 300 and apparatus 100 is the integration of measurement apparatus 2' with top-dressing device 4'. Referring to FIGS. 8A & 8B, an arm 51 connects frame 54 of measurement apparatus 2' to a trailer 50 upon which top-dressing device 4' is mounted. A single wheel 10' on measurement apparatus rolls on the ground surface as apparatus 300 moves, providing the drive to arm 16' through clutch 22'. Frame 54 is fixedly secured to arm 51. Alternatively frame 54 may be free-castering in relation to arm 51. Alternatively, other depth measuring devices could be substituted or combined with measurement apparatus 2'.

Apparatus 300 operates identically to apparatus 100, as described above, except that measurement apparatus 2' is integrated with top-dressing device 4', therefore both apparatus 2' and top-dressing device 4' are towed as a single unit behind a motive device (not shown). The process for sampling with apparatus 300 is identical to apparatus 100, except input device would likely require remote operation utilizing a wired or wireless connection. In addition, a vibratory device, similar to 27A as utilized in probe assembly 27 in apparatus 2, could be added to probe assembly 27'. Apparatus 300 is preferably towed, but alternatively could be pushed. Moreover, apparatus 300 could be self-propelled with the motive device comprising an engine or motor and a drive train carried on frame 54, arm 51 or trailer 50. In addition, apparatus 300 could be remotely controlled or operate independently through sensor-assisted navigation. Additionally, an optical sensor, similar to sensor 201 as utilized on frame 21 of apparatus 2 could be added to apparatus 300.

Figure 9:
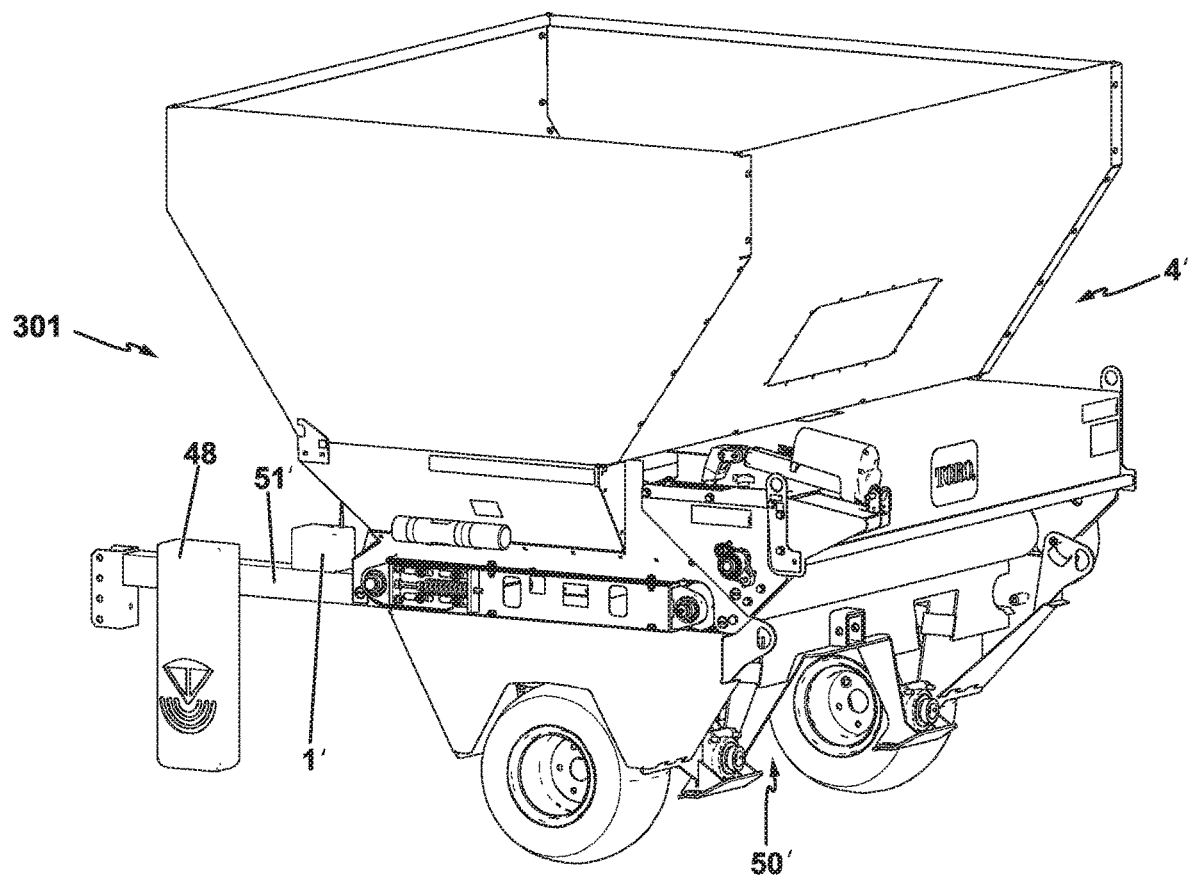
FIG. 9 is a perspective view towards the rear of a third embodiment of a mobile turf measurement apparatus according to this invention mounted on a towable top-dressing device.

A third embodiment of a mobile turf instrument apparatus according to this invention is illustrated in FIG. 9 as 301. Components of apparatus 301 that are the same as those of apparatus 300 will be referred to by the same reference numerals as used for those components of apparatus 100 but with a prime suffix being added, e.g. trailer 50' versus trailer 50. Much of apparatus 301 is the same as apparatus 300 including trailer 50' upon which top-dressing device 4' is mounted. Thus, only the differences between apparatus 301 and apparatus 300 will be specifically described hereafter.

The major difference between apparatus 301 and apparatus 300 is the use of an emitting and receiving sensor 48 in place of measurement apparatus 2'. Referring to FIG. 9, arm 51' connects sensor 48 to trailer 50' upon which top-dressing device 4' is mounted.

Apparatus 301 operates identically to apparatus 300, as described above, except that sensor 48 provides the input to the computer instead of measurement apparatus 2'. Sensor 48 may be any type of emitting and receiving sensor, including acoustic sensors and ground penetrating radar sensors. The use of such emitting and receiving sensors allow apparatus 301 to be used on both natural and synthetic turf. For example, ground penetrating radar can be used to measure the vertical profile of synthetic turf infill and an acoustic sensor can be used to detect the distance between a reference position (i.e. upper profile position) and a depression on the surface of natural turf (i.e. lower profile position). Output from either ground penetrating radar or an acoustic sensor can be processed by input device 1' to calculate an application rate necessary to fill depressions in the surface to the nominal or desired height. Sensor 48 allows near constant sampling to provide a precise calculation of needed particulate to reach the nominal or desired height.

Apparatus 300 is preferably towed, but alternatively, it could be pushed. Moreover, apparatus 301 could be self-propelled. In addition, apparatus 301 could be remotely controlled or operate independently through sensor-assisted navigation. Additionally, an optical sensor, similar to sensor 201 as utilized on frame 21 of apparatus 2 could be added to apparatus 301. In natural turf, an optical sensor would calculate the ratio of sand/soil to natural turf, rather than synthetic particulate 200D to visible synthetic fiber 200A.

Figure 10A:
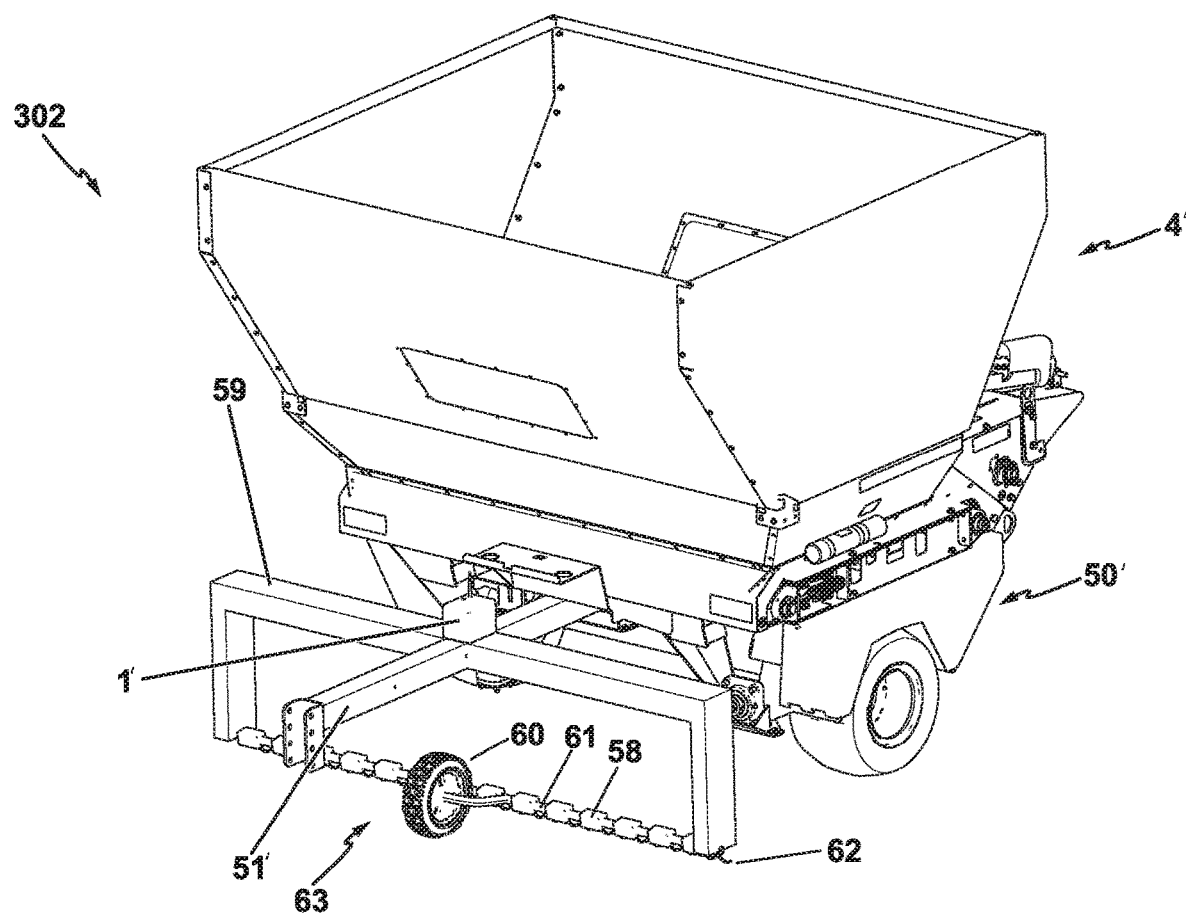
FIG. 10A is a perspective view toward the front of a fourth embodiment of a mobile turf instrument apparatus according to this invention mounted on a towable top-dressing device.

A fourth embodiment of a mobile turf instrument apparatus according to this invention is illustrated in FIG. 10 as 302. Components of apparatus 302 that are the same as those of apparatus 300 will be referred to by the same reference numerals as used for those components of apparatus 300 but with a prime suffix being added, e.g. trailer 50' versus trailer 50. Much of apparatus 302 is the same as apparatus 300 including trailer 50' upon which top-dressing device 4' is mounted. Thus, only the differences between apparatus 302 and apparatus 300 will be specifically described hereafter.

The major difference between apparatus 302 and apparatus 300 is the use of measurement apparatus 63 in place of measurement apparatus 2'. Measurement apparatus 63 may be used to measure surface profiles on both synthetic and natural turf Referring to FIGS. 10A & 10B, arm 51' connects measurement apparatus 63 to trailer 50' upon which top-dressing device 4' is mounted. Apparatus 63 is comprised of a frame 59, a pivot bar 61, sensing tines 62, sensors 58, reference wheel 60 and input device. As apparatus 302 moves across the surface, sensing tines 62, biased to contact the surface (i.e. lower profile position), independently pivot upon bar 61 across a range of undulations in the surface. In other words, sensing tines 62 are adapted to continually contact the surface despite differences in surface vertical elevation between a previous geographic location and a current geographic location.

The rotational position of sensing tines 62 on bar 61 are indicated by the electrical output of sensors 58. Each sensing tine 62 may activate its own dedicated sensor 58 or a plurality of side-by-side sensing tines 62 may activate a single sensor as a group. Sensors 58 are angular position sensors. However, other types of position measuring devices may be used to determine the angular position of the tines 62 on bar 61 such as Hall effect sensors. Alternatively, the vertical position of the surface-contact end of tines 62 could be indicated by linear position sensors such as linear potentiometers, membrane potentiometers, Hall effect sensors or draw wire potentiometers. The horizontal axis of reference wheel 60 is fixed in a vertical position in reference to bar 61.

Figure 10B:
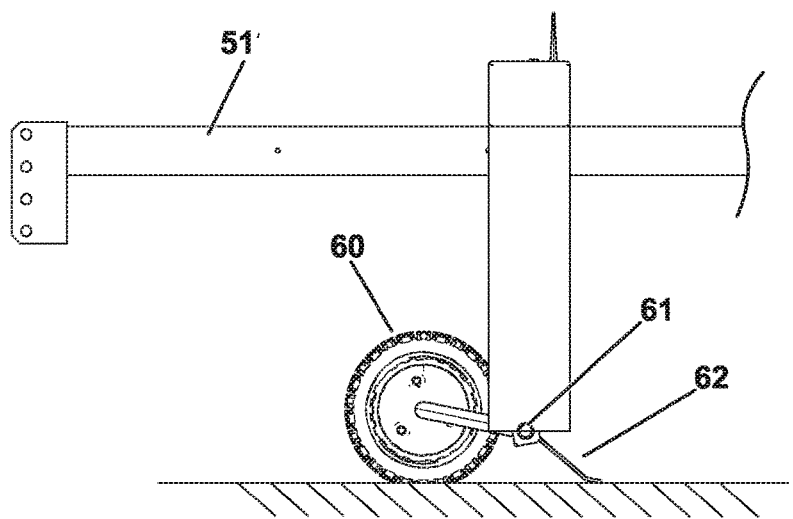
FIG. 10B is a side-elevation view of the mobile turf measurement apparatus of FIG. 10A.

The computer within input device is programmed to determine a reference position (i.e. upper profile position) when sensors 58 output a signal corresponding to a condition when the surface-contacting end of tines 62 and the lowest point of reference wheel 60 share the same vertical disposition as depicted in FIG. 10B. In this embodiment, the vertical height position as selected on input device 1' is in relation to the reference position. As apparatus 302 moves across the surface, the surface-contacting ends of the tines 62 will attempt to follow the surface contour as they are biased into contact with the surface. When the tines 62 encounter a high spot or bump in the surface, they will rotate in a counter-clockwise direction about the bar 61 and activate the corresponding sensor 58 to indicate a profile that is above the reference position. Similarly, when the tines 62 encounter a low spot or depression in the surface, they will rotate in a clockwise direction about the bar 61 and activate the corresponding sensor 58 to indicate a profile that is below reference position. The vertical positions of the surface profile as detected by each of the surface-contacting ends of tines 62 as read by sensors 58 are sent to the computer and recorded in input device. These readings are collectively analyzed by the computer in relation to an operator-selected application rate and the reference vertical profile height determined when the tips of all the tines 62 are in the same plane as the lowest point on wheel 60 to determine an application rate for infill material that is to be added to fill in any low spots in the surface. The computer then averages the readings from sensors 58 to determine an reading representing an average depression across the width of the tines 62 and outputs a correlating signal to top-dressing device 4'.

Apparatus 302 operates similarly to apparatus 300, as described above, except that measurement apparatus 63 provides the input to the computer instead of measurement apparatus 2'. Apparatus 302 is preferably towed, but alternatively, it could be pushed or be self-propelled. In addition, apparatus 302 could be remotely controlled or operate independently through sensor-assisted navigation. Additionally, an optical sensor, similar to sensor 201 as utilized on frame 21 of apparatus 2 could be added to apparatus 302. In natural turf, an optical sensor could be used to calculate the ratio of sand/soil to natural turf, rather than synthetic particulate 200D to visible synthetic fiber 200A.

Figure 11:
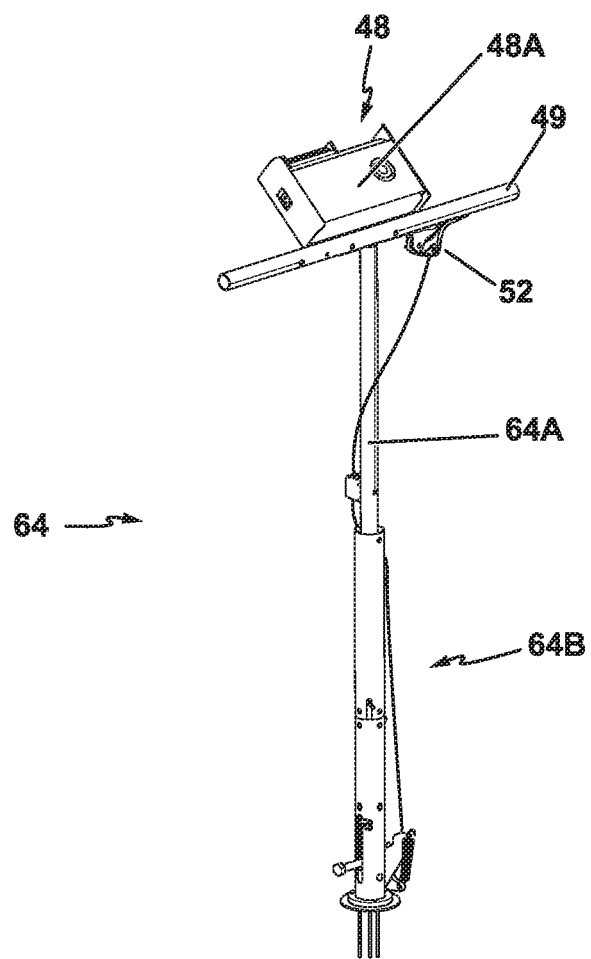
FIG. 11 is a perspective view of another embodiment of a measurement apparatus according to this invention.
Figure 12:
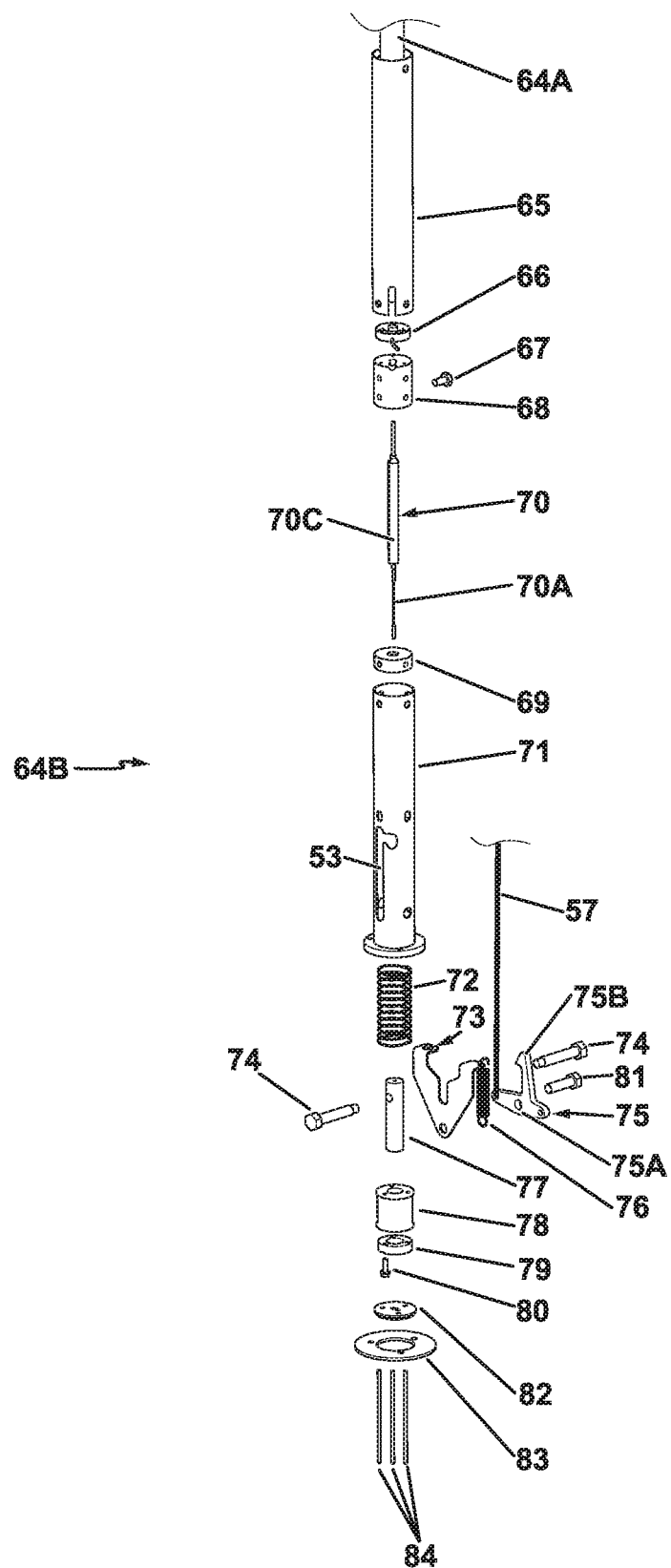
FIG. 12 is an exploded perspective view of the measurement apparatus in FIG. 11, particularly illustrating the probe assembly.
Figure 13:
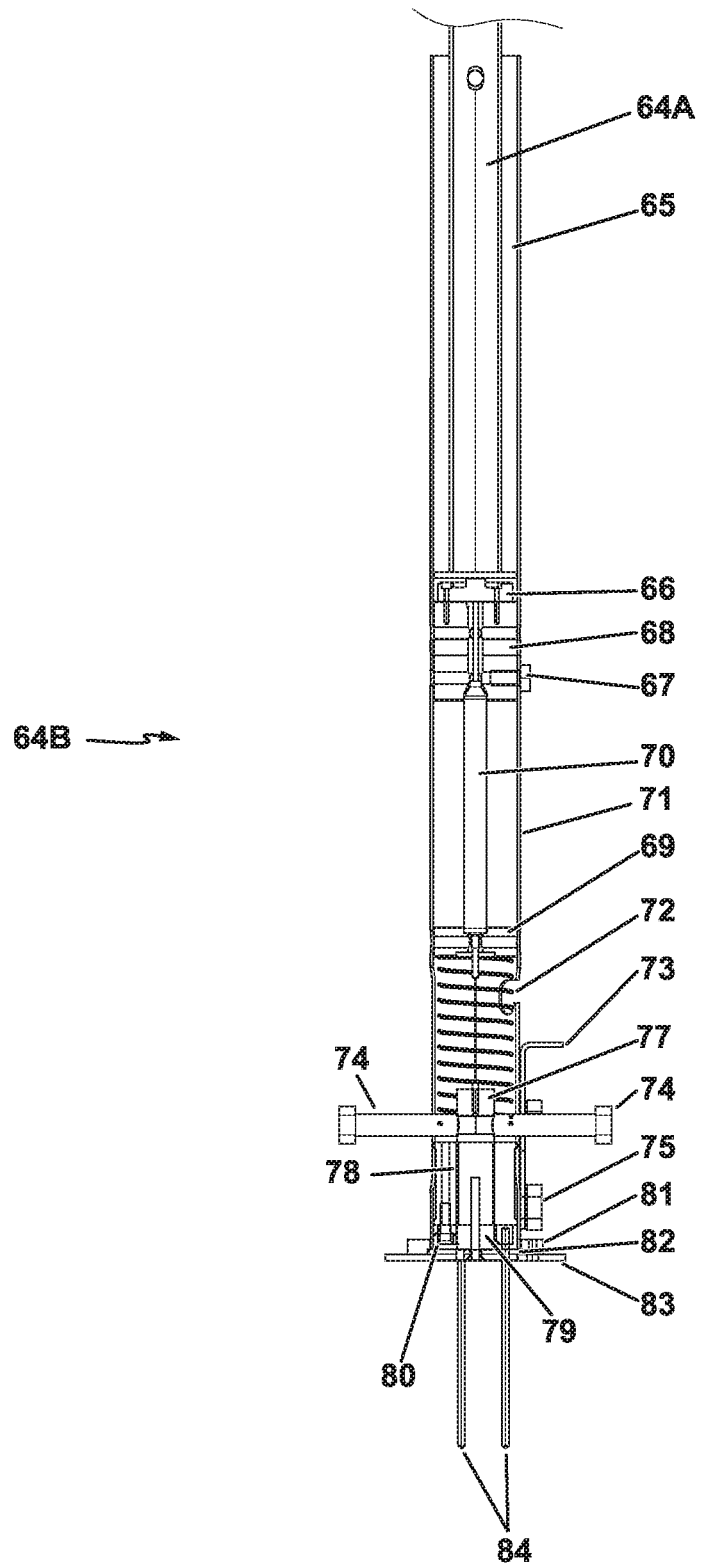
FIG. 13 is a side-elevation cross-sectional view of the probe assembly in FIG. 12.

Another embodiment of a measurement apparatus according to this invention is illustrated in FIGS. 11-13 generally as 64. Instead of being mounted on a wheeled apparatus, measurement apparatus 64 is a hand-held device. Processing unit 48, comprising a computer, memory and energy source, is secured to frame 64A and possesses an electronic display 48A, oriented at an acute angle from horizontal to provide a natural line of site from the vision of an operator using the apparatus. Alternatively, the display 48A of processing unit 48 may be at a different angle or the processing unit may reside in a portable electronic device with wireless connectivity, such as a smart phone or tablet computer.

Handle 49 provides a horizontal hand grip for an operator to hold apparatus 64. A trigger 52 is mounted to handle 49. Handle 49 is secured substantially perpendicular to the upper portion of a vertical frame 64A. A probe assembly 64B is secured to the lower portion of frame 64A.

Referring now to FIGS. 12 & 13, probe assembly 64B comprises an upper probe body 65 secured to the lower portion of frame 64A. Frame 64A further extends downward through an interior cavity of upper probe body 65, abutting against a load cell 66. A plug 68 is positioned within and secured to both the lower portion of upper probe body 65 and the upper portion of a lower probe body 71. Fasteners 67 pass through holes in both bodies 65 and 71 and thread into plug 68 to join the upper and lower probe bodies 65 and 71 together.

The inner wall of upper probe body 65 secures load cell 66 horizontally and load cell 66 is substantially secured vertically by the upper abutting frame 64A and lower abutting plug 68. A sensor 70 similar to sensor 38 is installed within lower probe body 71. The lower end of plug 68 is configured to receive the upper end of sensor body 70C and the lower end of sensor body 70C is received within an upper sensor receiver 69 to thereby mount sensor 70 within lower probe body 71. In one example, sensor 70 is a linear potentiometer. Alternatively, other length-measuring sensors may be used.

Both the lower end of plug 68 and upper sensor receiver 69 act to secure sensor 70 both horizontally and vertically within a cavity in lower probe body 71 by fasteners which secure upper sensor receiver 69 to body 71 so that sensor 70 is substantially vertical. A coil spring 72 is secured within body 71 and is vertically positioned between the lower end of upper sensor receiver 69 and the top of a lower sensor base 78. The vertically movable lower sensor shaft 70A of sensor 70 is threaded into a a lower sensor receiver 77 that is itself threaded into lower sensor base 78. Cross bolts 74 threadedly engage the curved surface of lower sensor receiver 77 at positions 180 degrees apart.

A spacer 79 is secured to lower sensor base 78 by fasteners 80. Cylindrically-shaped probes 84 are secured in a substantially vertical position in the lower end of spacer 79. An outer plate 83 concentrically surrounds an inner plate 82 and is also secured to the lower end of body 71. Probes 84 extend through holes in inner plate 82 and inner plate 82 has a lip that overlies an aperture in plate 83 which retains plate 82 atop plate 83. The lowest surfaces of plates 82 and 83 are substantially coplanar.

A centering plate 73 is externally fixed to body 71. A pivot bolt 81 pivotably couples a locking plate 75 to centering plate 73. The upper end of a tension spring 76 connects at one end to an upper tab on centering plate 73 and at the other end to one side of a lower arm 75 A on locking plate 75.

Spring 76 biases locking plate 75 to pivot horizontally about bolt 81 and capture the outward end of one of the bolts 74, when such bolt 74 is in the lower portion of a slot 53 provided on the lower probe body 71. While there are two bolts 74 received in two slots 53 on opposite sides of lower probe body 71, only one locking plate 75 is used interacting with only a single bolt 74. When bolt 74 is captured by the hook shaped latch 75B of locking plate 75, probes 84 are fixed in vertical position in relation to probe assembly 64B, frame 64A and handle 49. The lower end of a cable 57 is secured to the opposite side of arm 75 A of locking plate 75 from the side of arm 75A to which tension spring 76 is secured. The upper end of cable 57 is secured to trigger 52. Manual actuation of trigger 52 pulls cable 57 in an upward direction, thereby overcoming the locking force created by tension spring 76, to pivot latch 75B in a direction that releases bolt 74.

In normal operation of apparatus 64, the operator turns on processing unit 48, and waits for the visual indication that processing unit is ready for operation, as indicated on display 48A. After the operator ensures locking plate 75 has captured the adjacent bolt 74, the operator then pushes down on handle 49 to push probes 84 into the turf profile. As the operator pushes down on handle 49, the signal from load cell 66 is sampled by processing unit 48 and converted into a correlating force which is depicted on display 48A. The operator waits for such force to rise to a predetermined level and secondarily feels for significant resistance to further pushing down on handle 49 to indicate that a sufficient downward force has been applied to probes 84 for the lower end of probes 84 to have reached backing 200C.

Once the necessary force has been applied to indicate that probes 84 have descended through the depth of the turf profile and reached the underlying backing 200C in a synthetic turf surface, the operator actuates trigger 52 to swing latch 75B off bolt 74 as previously described. This allows handle 49, frame 64A, and probe assembly 64B including plates 82 and 83 to uniformly descend downward relative to tines 84 until plates 82, 83 contact the top surface of the particulate profile 200B in a synthetic turf surface. As plates 82, 83 descend, sensor shaft 70A slides upward into sensor body 70C.

While trigger 52 is actuated and the above operation is taking place, the computer repeatedly samples and logs output from sensors 66 and 70. When sensor 66 outputs a value correlating to a force required to apply two pounds per square inch to the coplanar surfaces of plates 82, 83, the computer is programmed to select the smallest output value of sensor 70 to convert to a vertical distance. Alternatively, the computer could be programmed to select the maximum output value of sensor 70, to select a series of different output values, or to perform a statistical analysis of a series of different output values. Moreover, the operator could directly instruct the processing unit to sample the output from sensor 70 at a specific time. The processing unit then records the vertical distance as an indication of the depth of particulate profile at the sampled spot, e.g. the depth between the upper profile position indicated by the plates 82, 83 and the lower profile position indicated by the tips of the tines 84. The operator then lifts up on handle 49, pushes down on bolt 74 till bolt 74 is captured by latch 75B of locking plate 75, at which point the apparatus is ready to repeat the process after the operator moves to a different sampling location on the turf surface.

For each sampling of sensor 70, processing unit 48 samples the output of a geographic location sensor located in processing unit 48. The geographic location sensor is a global positioning sensor (GPS), but other triangulation or geographic locating systems could be used. The vertical distance, downward force, and geographic location data comprise a collective data set for each sampled location and may be stored in permanent or removable memory in processing unit 48 or may be transmitted wirelessly to another data storage device. The collective data set could be displayed in a geographic representation. In addition, the collective data set could be sent to an input device similar to input device 1' which may output signals to a variable rate top dresser, similar to top-dressing device 4'. Additionally, an optical sensor, similar to sensor 201 as utilized on frame 21 of apparatus 2 could be added to apparatus 64.

The modifications and comments described above with respect to diameter of probes 28 and the pressure applied by probes 28 of probe assembly 27 on measurement apparatus 2 are intended to apply equally to probe assembly 64B.

Figure 14:
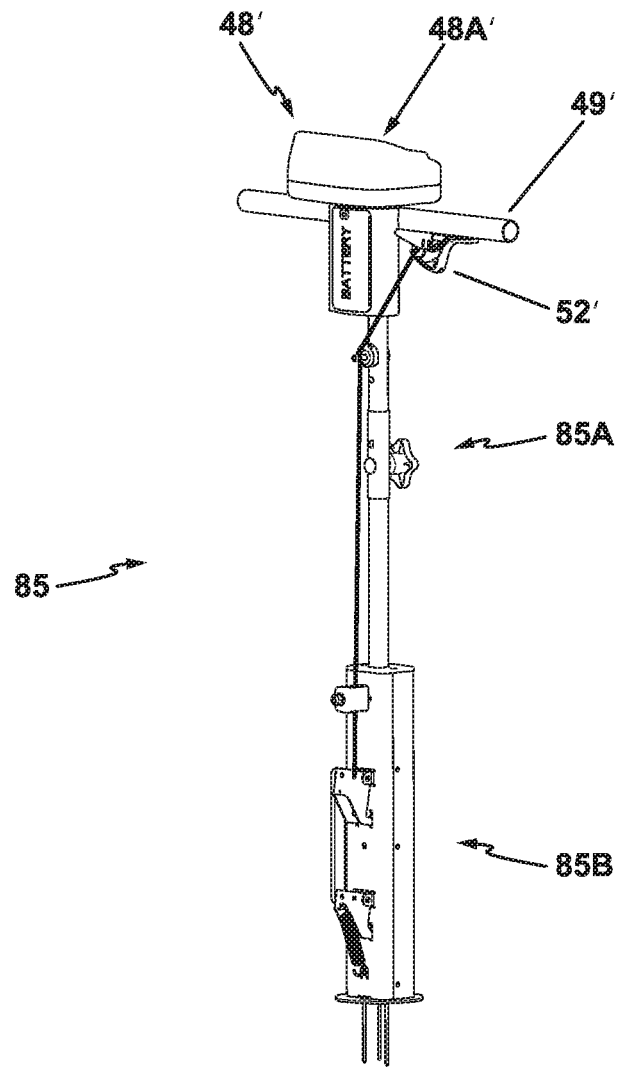
FIG. 14 is a perspective view of a another embodiment of a measurement apparatus according to this invention.
Figure 15:
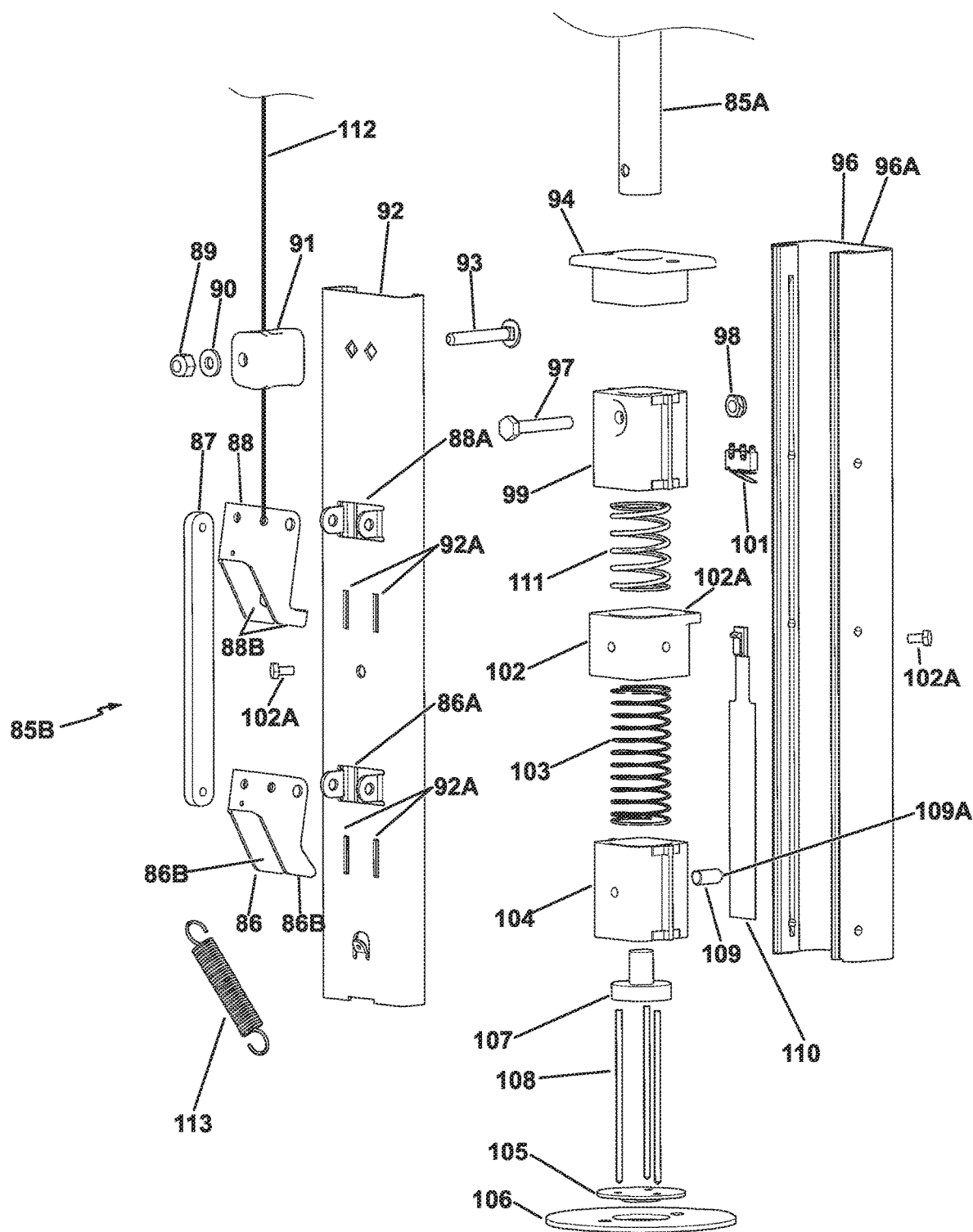
FIG. 15 is an exploded perspective view of the measurement apparatus in FIG. 14, particularly illustrating the probe assembly.
Figure 16:
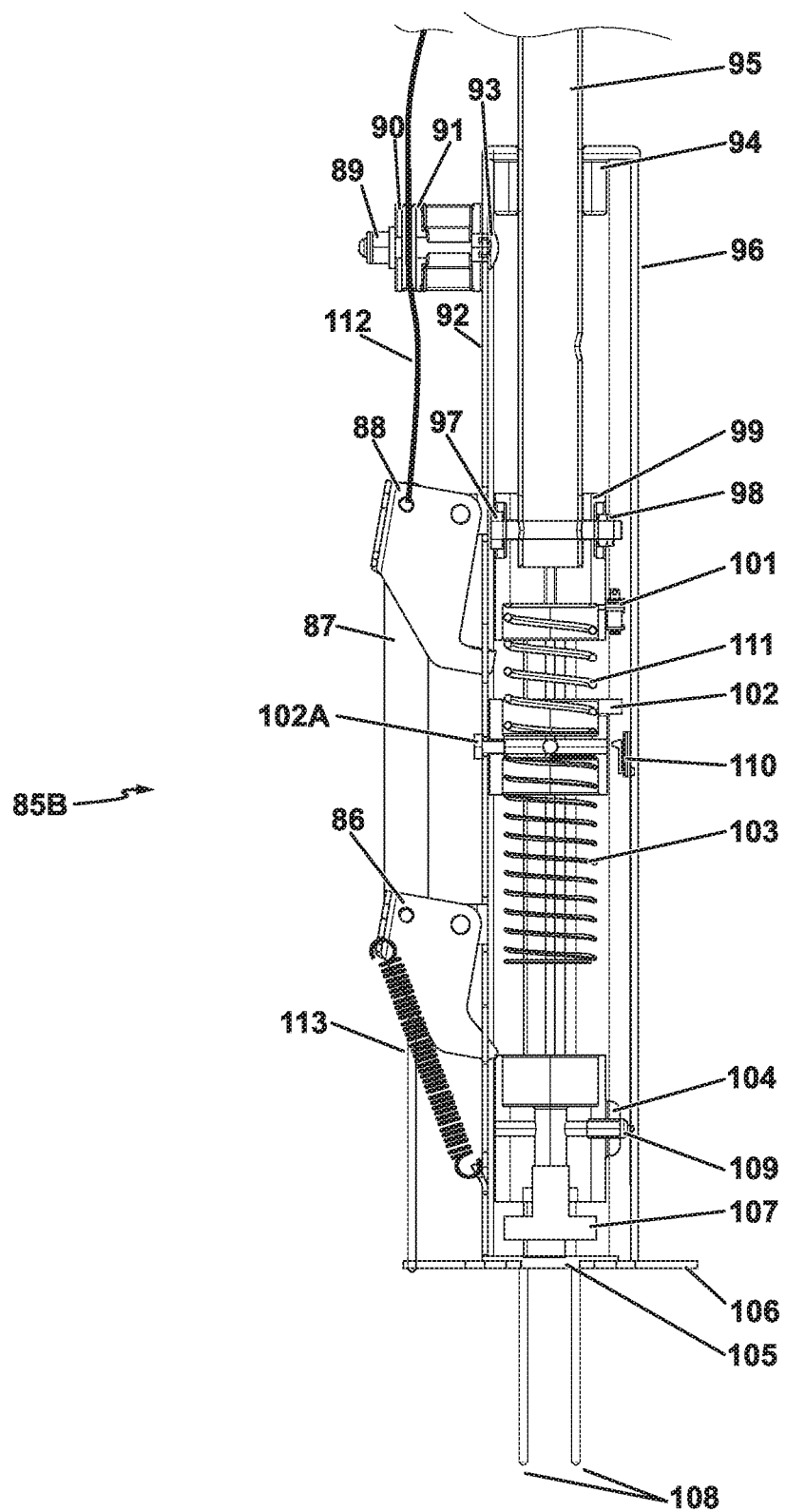
FIG. 16 is a side-elevation cross-sectional view of the probe assembly in FIG. 15.

Another embodiment of a measurement apparatus according to this invention is illustrated in FIGS. 14-16. Components of apparatus 85 that are the same as those of apparatus 64 will be referred to by the same reference numerals as used for those components of apparatus 64 but with a prime suffix being added, e.g. handle 49' versus handle 49.

Handle 49' provides a horizontal hand grip for an operator to hold apparatus 85. Trigger 52' is mounted to handle 49'. Handle 49' is secured substantially perpendicular to the upper portion of vertically-oriented frame 85A. A probe assembly 85B is secured to the lower portion of frame 85A.

Referring now to FIGS. 15 & 16, the lower portion of frame 85A passes through an opening in a guide 94 and is secured to sliding spacer 99 using a fastener 97 and a nut 98. Sliding spacer 99 is restrained horizontally within a surrounding front body 92 and rear body 96. Bodies 92, 96 are each substantially U-shaped. Bodies 92, 96 are secured to one another to collectively form a square tube. A guide 94 substantially encloses the upper end of the tube created by bodies 92, 96 except for the opening in which frame 85A passes through.

The lower surface of sliding spacer 99 has a cylindrical depression adapted to receive an upper portion of coil spring 111. A stationary spacer 102, is horizontally and vertically restrained by fasteners 102A which pass through holes in bodies 92, 96 and thread into spacer 102. The upper end of spacer 102 has a horizontally extending platform 102A. A switch 101 is secured to the vertical side of sliding spacer 99. Switch 101 is positioned above and in vertical alignment with horizontal platform 102 A on stationary spacer 102.

The upper surface of stationary spacer 102 also has a cylindrical depression adapted to receive a lower portion of coil spring 111. The lower surface of stationary spacer 102. has a cylindrical depression adapted to receive an upper portion of a second coil spring 103. A second sliding spacer 104, like spacer 99, is horizontally captured within the tube formed by bodies 92 and 96 but is positioned below stationary spacer 102 rather than being above stationary spacer 102 as is the case for the first sliding spacer 99. The upper surface of second sliding spacer 104 has a cylindrical depression adapted to receive a lower portion of the second coil spring 103.

The upper end of a receiving spacer 107 is secured to the lower end of second sliding spacer 104. Cylindrically-shaped probes 108 are secured in a substantially vertical position in the lower end of receiving spacer 107. Probes 108 extend through holes in inner plate 105 and inner plate 105 is secured to outer plate 106. Outer plate 106 concentrically surrounds the lowest surface of inner plate 105 and is secured in any suitable manner to the lower end of the tube formed by bodies 92, 96. The lowest surfaces of plate 105 and plate 106 are substantially coplanar.

A sensor 110 is secured to the interior surface of the base wall 96A of body 96 and extends therealong in a vertical direction. In one example, sensor 110 is a linear potentiometer. Alternatively, other length-measuring sensors may be used. Sensor 110 has a substantially cuboid composition, with a thickness shorter than width, and its width is much shorter than the length of sensor 110. The length runs in a substantially vertical direction. A wiper 109 has a proximate end secured to the vertical side of second sliding spacer 104 and a distal end 109 A which contacts the largest vertical surface of sensor 110 It is the vertical motion of wiper 109 along sensor 110 that provides the vertical distance measurement to be described hereafter.

The upper end of a cable 112 is secured to trigger 52'. Cable 112 extends downward from trigger 52' and is secured to body 92, by a cable block 91, bolt 93, washer 90 and nut 89. The lower end of cable 112 is secured to an upper latch 88 which is horizontally pivotably secured to body 92 between the ears of a yoke 88A. A connecting link 87 pivotally secures upper latch 88 to a lower latch 86 that is substantially identical to upper latch 88. Lower latch 86 is horizontally pivotably secured to body 92 between the ears of a yoke 86 A. A biasing spring 113 is connected between lower latch 86 and a lower portion of body 92. Latches 86, 88 have tabs 86B, 88B which latch into slots 92A in body 92.

Apparatus 85 is in a resting state when trigger 52' is not actuated. In the resting state, there is no force acting on probes 108 and probe assembly 85B. In this resting state, spring 113 biases latches 86, 88 to an engaged position in which tabs 86B, 88B pass through both sets of slots 92 A in body 92 to prevent lower sliding spacer 104 from moving vertically upwardly and to prevent upper sliding spacer 99 from moving vertically downwardly.

In the resting state described above with latches 86 and 88 engaged in body 92, probes 108 are fixed in vertical position relative to probe assembly 85B, frame 85A and handle 49'. Actuation of trigger 52' pulls cable 112 in an upward vertical motion. This pivots tabs 86B, 88B of latches 86, 88 out of slots 92A in which they had previously been engaged to disengage latches 86, 88. This allows lower spacer 104 to slide vertically upwardly and upper spacer 99 to slide vertical downwardly.

In normal operation of apparatus 64, the operator turns on processing unit 48' and waits for the visual indication that processing unit is ready for operation as indicated on display 48A'. Next, the operator actuates and releases trigger 52' to ensure both springs 103, 111 are in their extended positions. With trigger 52' released, the operator proceeds to push down on handle 49', thereby pushing probes 108 into the turf profile, until the operator feels significant resistance. When the operator feels such resistance, the operator actuates and holds trigger 52' in the actuated state which disengages latches 86, 88 to allow plate 106 along with bodies 92, 96 to move downward toward the surface of the turf.

During the downward movement of plate 106, spring 103 compresses, and lower sliding spacer 104 along with wiper 109 move upward, while distal end 109A of wiper 109 maintains contact with sensor 110. Also during this downward movement of plate 106, spring 111 compresses and upper sliding spacer 99 along with switch 101 moves downward in relation to bodies 92, 96 and to the platform 102A on stationary spacer 102. At a distance just prior to contact between the lower end of spacer 99 and the upper end of spacer 102, switch 101 contacts platform 102A on spacer 102. When this happens, switch 101 sends a signal to processing unit 48' to sample the output of sensor 110 and convert that output to a vertical distance. This process ensures that a consistent force (as supplied by spring 111 compressed to an exact distance) is applied to plates 105, 106 between different measurements and different operators.

Alternatively, an adjustment screw threadably engaged to the upper surface of the platform 102A on spacer 102 may provide the contacting surface by which switch 101 is actuated. An adjustment screw as described would provide a range of application forces exerted by spring 111, as the screw is adjusted in height relative to the surface of the platform 102A on spacer 102. The operator then lifts on handle 49', removing probes 108 from contact with the ground (which allows springs 111, 103 to extend to their normal resting positions) and releases trigger 52', at which point the apparatus is ready to be moved to a different location to repeat the process. Alternatively, a vibratory device, as utilized in on probe assembly 27 in apparatus 2, could be added to apparatus 85.

For each sampling of sensor 110 at a different location in the area of turf being measured, processing unit 48' samples the output of a geographic location sensor located in processing unit 48'. The geographic location sensor is a global positioning sensor (GPS), but other triangulation or geographic locating systems could be used. The vertical distance and geographic location data comprise a collective data set and may be stored in permanent or removable memory in processing unit 48' or may be transmitted wirelessly to another data storage device. The collective data set could be displayed in a geographic representation. In addition, the collective data set could be sent to an input device similar to input device 1' which may output signals to a variable rate top dresser, similar to top-dressing device 4'.

Additionally, an optical sensor, similar to sensor 201 as utilized on frame 21 of apparatus 2 could be added to apparatus 85.

Figure 17:
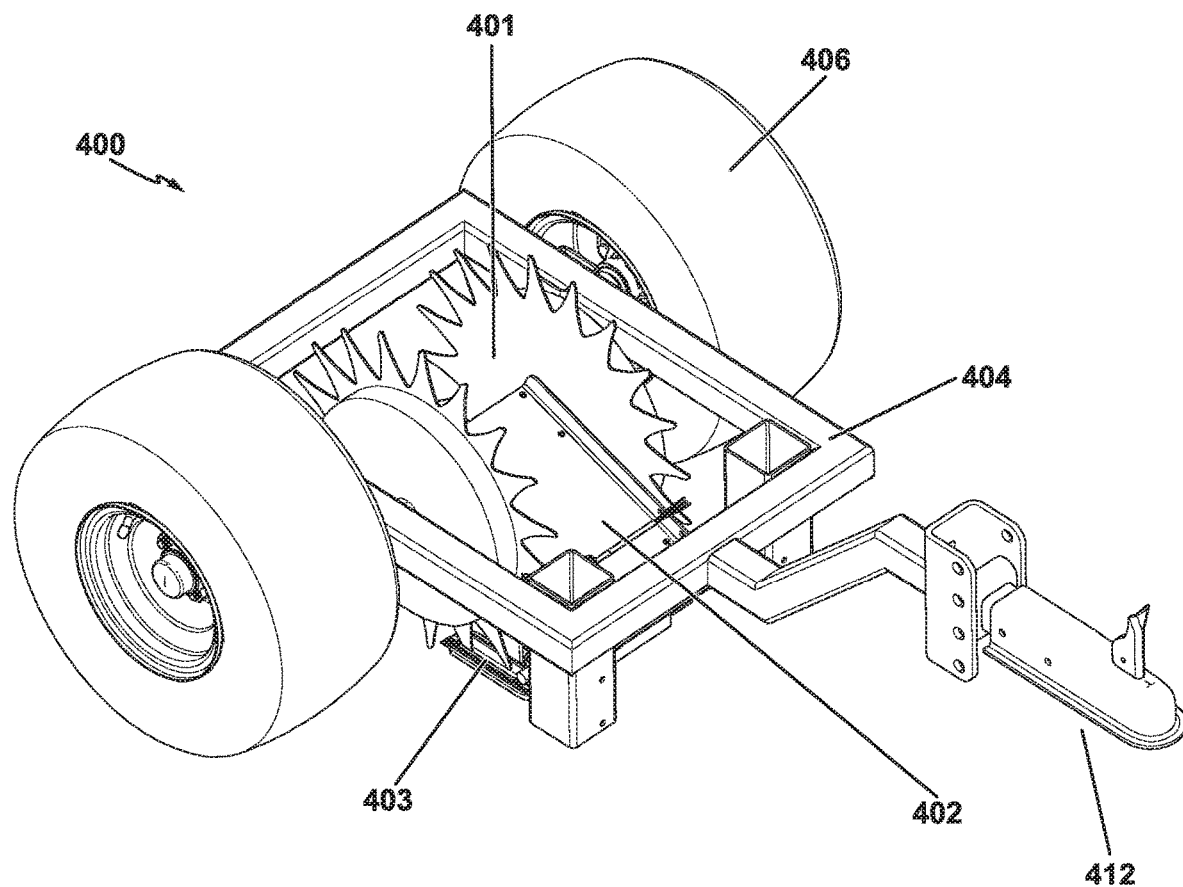
FIG. 17 is a perspective view of a another embodiment of a mobile turf measurement apparatus according to this invention.
Figure 18:
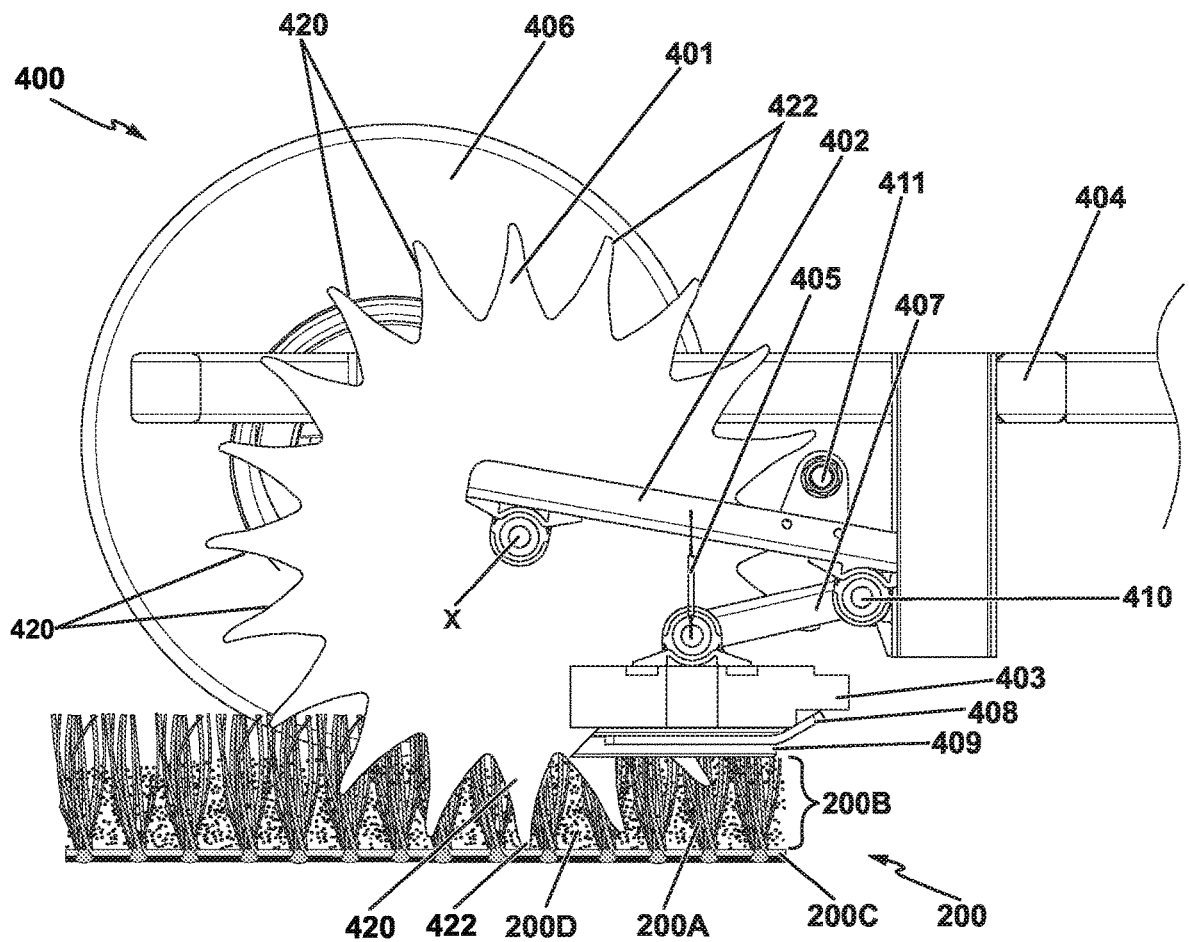
FIG. 18 is a side-elevation cross-sectional view of the measurement apparatus in FIG. 17, particularly illustrating the probe assembly.

Another embodiment of a measurement apparatus according to this invention is illustrated in FIGS. 17 & 18. Measurement apparatus 400 intermittently samples the height of profile 200B as it moves across the surface. Apparatus 400 is acted upon by a motive device (not shown) through arm 412, which is secured to frame 404.

A probe wheel 401 comprises a circular plate having a toothed outer diameter. Probe wheel 401 is rotatably secured to a platform 402 for rotation about a substantially horizontal axis of rotation indicated as x in FIG. 18. There may be a single probe wheel 401 or duplicate side-by-side probe wheels 401 that rotate about a common axis. In the embodiment of FIGS. 17 and 18, there are two side-by-side probe wheels 401.

The radially extending teeth provided on the outer diameter of probe wheel 401 form probes 420 that rotate in substantially the same rotational direction as wheels 406 when frame 404 moves across the surface. Probe wheel 401 is not positively powered but rotates simply because of the contact between probe wheel 401 and the turf surface and the forward motion of frame 404. As shown in FIG. 18, probe wheel 401 engages the turf profile 200B, with the tips of probes 420 contacting the upper surface of backing 200C. It is preferable for the surface 422 of the probe tips, namely the surface which first contacts the surface of the synthetic turf during rotation of probe wheel 401, to possess a rounded leading edge to prevent the probe tips from penetrating backing 200C.

Weight may be added to probe wheel 401 to increase probe tip pressure against backing 200C. Alternatively, an actuator or spring could be secured to wheel 401 and frame 404 to increase probe tip pressure. A sensor 411 is secured to platform 402 and is positioned to detect the presence of a probe tip by detecting the presence of a ferrous object. Platform 402 is pivotally secured to a pivot shaft 410 carried on frame 404. Pivot shaft 410 is located on the opposite end of platform 402 from the rotational axis x where probe wheel 401 is rotatably journalled on platform 402. An arm 407 is fixed in position to bar 410 and the opposing end of arm 407 is pivotably secured to skid 408.

The leading edge of skid 408, in relation to the direction of travel, is positioned at a substantially acute angle in relation to the upper surface of profile 200B. The lowest surface of skid 408 is substantially a flat plane which slides along the upper surface of profile 200B, providing the reference point for the upper position of profile 200B. A weight 403 may be added to skid 408 to bias the lowest surface of skid 408 to contact the upper surface of profile 200B to achieve a contact pressure from 0.5 PSI to 8 PSI to obtain repeatable and accurate vertical distance measurements. Alternatively, a spring or actuator may bias the lowest surface of skid 408 to contact the upper surface of profile 200B.

As shown in FIGS. 17 and 18, skid 408 has a vertical opening 409 through which the tips of probes 420 of probe wheel 401 are consecutively received as wheel 401 rotates. The sides of the vertical opening 409 are wedge shaped. As skid 408 slides along the surface, the wedge-shaped sides of opening 409 serves to position the upper ends of turf fibers 200A horizontally away from the vertical opening. In other words, fibers 200A are pushed in a direction perpendicularly outwardly to each side of the vertical circular plane of probe wheel 401. This clears a path for the tips of probes 420 to enter the turf profile, the path being substantially cleared of fibers 200A.

During operation the tips of probes 420 of probe wheel 401 pass through the wedge-shaped opening 409 of skid 408 rotating into contact with backing 200C. When a sensor 411 senses the presence of a probe tip, sensor 411 sends a nearly instantaneous signal to an input device, like input device 1, having a computer or processing unit 48. Sensor 411 and the probe tips on wheel 401 are positioned so that a probe tip will be within the sensing range of sensor 411 when another probe tip is in contact with backing 200C. The computer within the input device is programmed to nearly instantaneously sample sensor 405 when a signal is received from sensor 411. Sensor 405 is sampled for a value which represents the lowest vertical position of a probe tip (i.e. lower profile position) and the vertical position of the lowest surface of skid 408 (i.e. upper profile position), which represents the vertical height of profile 200B. Sensor 405 is a linear potentiometer. Alternatively, sensor 405 could be another position sensing device like a membrane potentiometer, draw wire transducers or Hall effect sensor. Moreover, the relative position of the probe tips of probe wheel 401 and the lowest surface of skid 408 could be detected with a rotational sensing device secured to shaft 410 and platform 402.

Referring to FIG. 18, clockwise rotational input to shaft 410 rotates the shaft 410 clockwise causing arm 407 to contact and rotate platform 402 clockwise. This will raise probe wheel 401 and skid 408. Counter-clockwise rotation will reverse the process and lower wheel 401 and skid 408. Alternatively, arm 407 of skid 408 may be lifted via a linear actuator secured to the frame to achieve similar results as the previously described rotational actuation.

Alternatively, frame 404 could be pushed by the separate vehicle rather than being towed. Moreover, frame 404 could be self-propelled with the motive device comprising an engine or motor carried on frame 404. In addition, frame 404 could be remotely controlled or operate independently through sensor-assisted navigation.

Alternatively, a vibratory device, as utilized in on probe assembly 27 in apparatus 2, could be added to apparatus 400.

For each sampling of sensor 405, an input device samples the output of a geographic location sensor located in the input device (similar to processing unit 48). The geographic location sensor is a global positioning sensor (GPS), but other triangulation or geographic locating systems could be used. The vertical distance and geographic location data comprise a collective data set and may be stored in permanent or removable memory in the input device or may be transmitted wirelessly to another data storage device. The collective data set could be displayed in a geographic representation. In addition, the collective data set could be sent to an input device similar to input device 1' which may output signals to a variable rate top dresser, similar to top-dressing device 4'. Additionally, an optical sensor, similar to sensor 201 as utilized on frame 21 of apparatus 2 could be added to apparatus 400.

Apparatus 400 may be used in substitution of apparatus 2 on apparatus 100, with arm 411 connecting to structure 5. Additionally, apparatus 400 may be used in substation of apparatus 2' on apparatus 300, through securement of frame 404 to arm 51.

Figure 19:
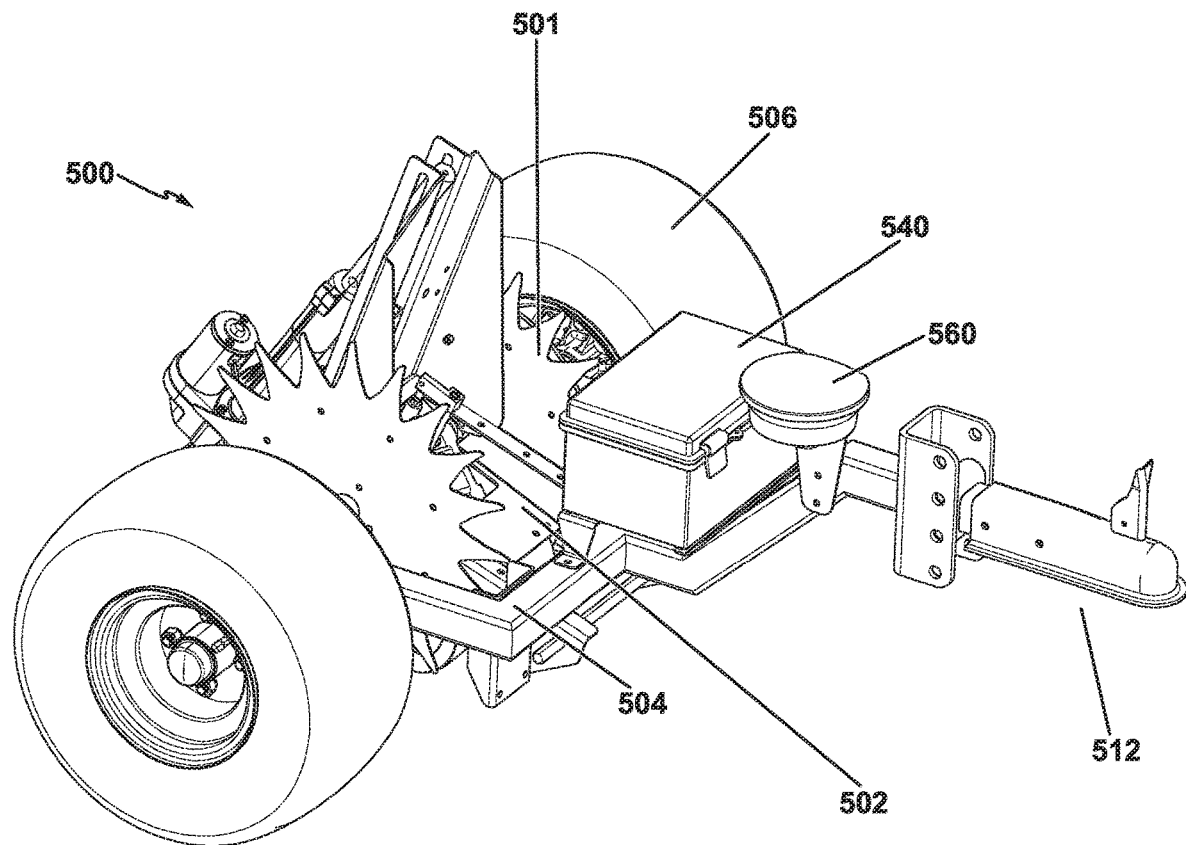
FIG. 19 is a perspective view of a another embodiment of a mobile turf measurement apparatus according to this invention.
Figure 20:
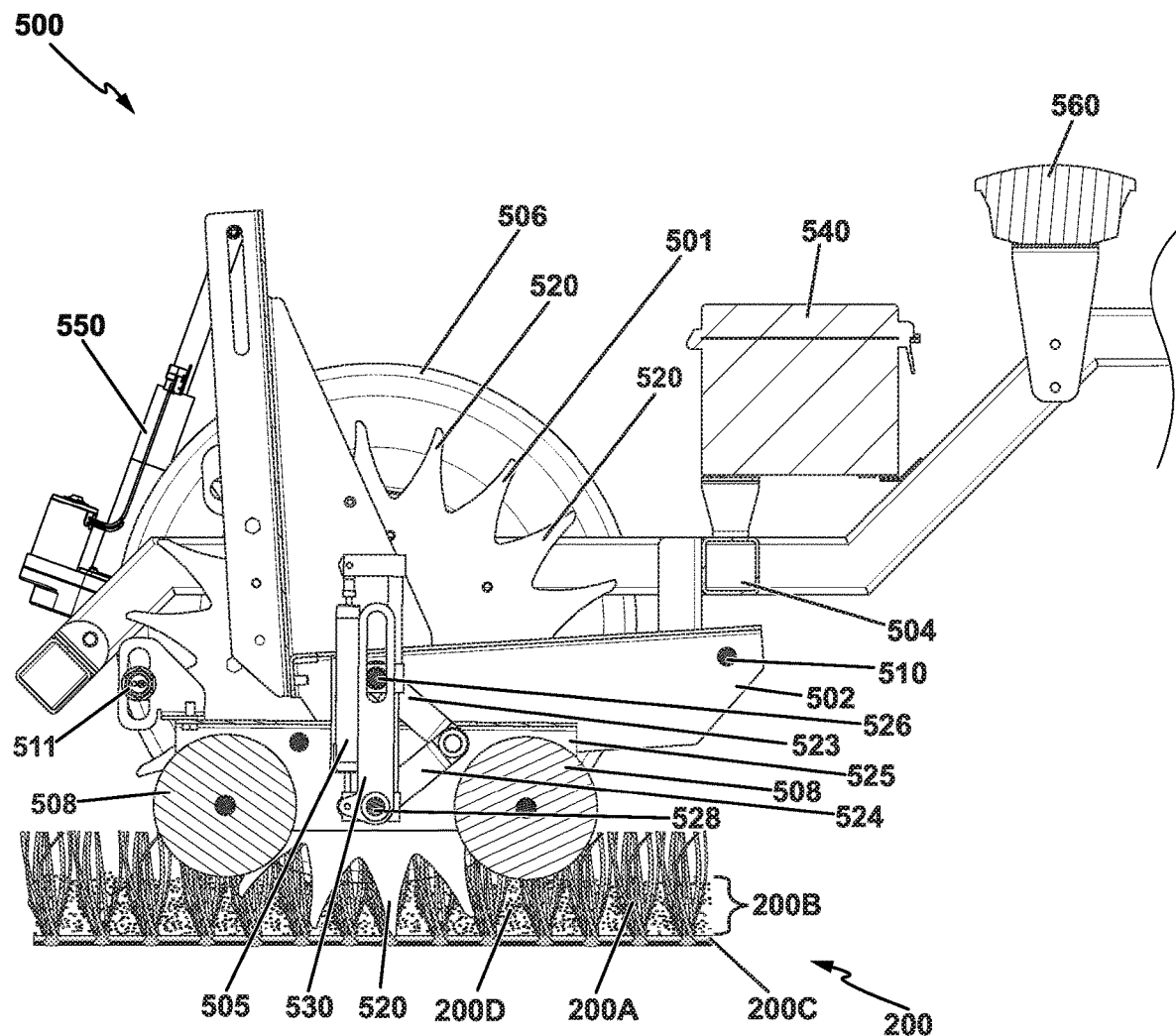
FIG. 20 is a side-elevation cross-sectional view of the measurement apparatus in FIG. 19, particularly illustrating the probe assembly.

Another embodiment of a measurement apparatus according to this invention is illustrated in FIGS. 19 & 20. Measurement apparatus 500 intermittently samples the height of profile 200B as it moves across the surface. Apparatus 500 is acted upon by a motive device through arm 512, which is secured to frame 504. Measurement apparatus 500 is similar to measurement apparatus 400 in using various rotatable probe wheels. Thus, component of measurement apparatus 500 that are the same as corresponding components of apparatus 400 will be referred to by the same reference numerals used for apparatus 400 but with a 500 prefix, i.e. probe wheel 501 rather than probe wheel 401. Thus, the common features between apparatus 500 and apparatus 400 will not be repeated herein for the sake of brevity. Instead, only the significant differences will be describe.

Turning to such differences, an upper end of a first arm 523 is pivotably secured by a pivot 526 to a platform 502. Pivot 526 is coaxially aligned with the rotational axis x of wheel 501. The upper end of a second arm 524 is pivotably secured to the lower end of arm 523. The lower end of second arm 524 is pivotably secured at a lower end to an assembly 525 through a pivot 528. A sensor assembly 530 is pivotably secured to assembly 525 at pivot 528 and slidably secured to platform 502 at pivot 526, which allows the sensor assembly 530 to extend and retract in a substantially vertical direction. A sensor 505 has two opposing ends which are secured to sensor assembly 530 and configured to measure the distance between pivots 526, 528 which represent the vertical distance of the infill profile 200B.

Pivot 528 is positioned between a pair of rollers 508 carried on assembly 525. Rollers 508 roll along the upper surface of profile 200B. The lowest points of rollers 508 provide the reference plane or reference surface for the upper position of profile 200B. In one example, rollers 508 maintain a contact pressure, with the upper surface of profile 200B, from 0.5 PSI to 8 PSI to obtain repeatable and accurate vertical distance measurements. Weight may be added to rollers 508 or to assembly 525 to vary the contact pressure. Alternatively, a spring or actuator may bias rollers 508 to contact the upper surface of profile 200B. Rollers 508 are positioned between wheels 501, but alternatively, rollers 508 may be arranged outside of wheels 501.

During operation the tips of probes 520 of wheel 501 rotate into contact with backing 200C. When sensor 511 senses the presence of a probe tip, sensor 511 sends a nearly instantaneous signal to an input device 540 having a computer, like input device 1 or processing unit 48. Sensor 511 and the tips of probes 520 on wheels 501 are positioned so that a probe tip will be within the sensing range of sensor 511 when another probe tip is in contact with backing 200C. The computer within input device 540 is programmed to nearly instantaneously sample sensor 505 upon receiving a signal from sensor 511. Sensor 505 is sampled for a value which represents the lowest vertical position of a probe tip (i.e. lower profile position) and the vertical position of the lowest surface of rollers 508 (i.e. reference surface, upper profile position), which represents the vertical height of profile 200B. Sensor 505 is a linear potentiometer. Alternatively, sensor 505 could be another position sensing device like a membrane potentiometer, draw wire transducers or Hall effect sensor. Moreover, the relative position of the probe tips of wheel 501 and the lowest surface of rollers 508 could be detected with a rotational sensing device secured to arms 523, 524.

Referring to FIGS. 19 and 20, extension of actuator 550, pivots platform 502 clockwise, which raises rollers 508, once pivot 526 reaches the maximum length allowed by sensor assembly 530. Retraction of actuator 550 will reverse the process and lower rollers 508.

Alternatively, frame 504 could be pushed by the separate vehicle rather than being towed. Moreover, frame 504 could be self-propelled with the motive device comprising an engine or motor carried on frame 504. In addition, frame 504 could be remotely controlled or operate independently through sensor-assisted navigation.

Alternatively, a vibratory device, as utilized in on probe assembly in apparatus 2, could be added to apparatus 500.

For each sampling of sensor 505, input device 540 samples the output of a geographic location sensor 560 (similar to processing unit 48). The geographic location sensor 560 is a global positioning sensor (GPS), but other triangulation or geographic locating systems could be used. The vertical distance and geographic location data comprise a collective data set and may be stored in permanent or removable memory in input device 540 or may be transmitted wirelessly to another data storage device. The collective data set could be displayed in a geographic representation. In addition, the collective data set could be sent to an input device similar to input device 1' which may output signals to a variable rate top dresser, similar to top-dressing device 4'. Additionally, an optical sensor, similar to sensor 201 as utilized on frame 21 of apparatus 2 could be added to apparatus 500.

Apparatus 500 may be used in substitution of apparatus 2 on apparatus 100, with arm 512 connecting to structure 5. Additionally, apparatus 500 may be used in substitution of apparatus 2' on apparatus 300, through securement of frame 504 to arm 51.

Various modifications of this invention will be apparent to those skilled in the art. Thus, this invention is not limited to the specific details of the embodiments disclosed herein, but only by the appended claims.

The invention claimed is:

1. A method for measuring a turf infill profile of an infill particulate material lying on a backing material of a synthetic turf surface and for adding infill particulate material to low spots in the turf infill profile, which comprises:
    (a) providing a measurement assembly for measuring the turf infill profile at a plurality of sampled locations in the synthetic turf surface;
    (b) providing a top dresser that carries a supply of infill particulate material and that is capable of applying additional infill particulate material to the synthetic turf surface;
    (c) moving the measurement assembly over the synthetic turf surface and determining if low spots exist in the turf infill profile at the sampled locations; and
    (d) moving the top dresser over the synthetic turf surface and, for the sampled locations at which low spots have been determined to exist, operating the top dresser to apply additional infill particulate material to the low spots.

2. The method of claim 1, wherein the measurement assembly and the top dresser are moved in concert with one another over the synthetic turf surface, and wherein operating the top dresser to apply additional infill particulate material to any given low spot occurs substantially simultaneously with the determination by the measurement assembly that the given low spot is present.

3. The method of claim 1, wherein the low spot determining step comprises measuring a height of the infill particulate material and comparing the measured height to a desired or nominal height of the infill particulate material.

4. The method of claim 1, wherein the step of providing a top dresser includes providing a vehicle including the top dresser and wherein the step of providing a measurement assembly includes providing a mobile measurement apparatus operably coupled to the vehicle.

5. The method of claim 1, wherein the step of providing a measurement assembly includes providing an optical sensor for measuring an amount of visible infill particulate and an amount of visible backing material.

6. The method of claim 3, further including allowing a user to input the desired or nominal height of the infill particulate material for use in the low spot determining step.

7. The method of claim 5, wherein the step of determining if low spots exist in the turf infill profile is additionally based on a ratio of the amount of visible infill particulate to the amount of visible backing material.

8. A method for measuring a turf infill profile of an infill particulate material lying on a backing material of a synthetic turf surface and for adding infill particulate material to low spots in the turf infill profile, which comprises:
    (a) providing a vehicle including a top dresser that carries a supply of infill particulate material and that is capable of applying additional infill particulate material to the synthetic turf surface;
    (b) providing a mobile measurement apparatus operably coupled to the vehicle, the mobile measurement apparatus including a measurement assembly for measuring the turf infill profile at a plurality of sampled locations in the synthetic turf surface;
    (c) moving the measurement assembly over the synthetic turf surface and determining if low spots exist in the turf infill profile at the sampled locations; and
    (d) moving the top dresser over the synthetic turf surface and, for the sampled locations at which low spots have been determined to exist, operating the top dresser to apply additional infill particulate material to the low spots.

9. The method of claim 8, wherein the measurement assembly and the top dresser are moved in concert with one another over the synthetic turf surface, and wherein operating the top dresser to apply additional infill particulate material to any given low spot occurs substantially simultaneously with the determination by the measurement assembly that the given low spot is present.

10. The method of claim 8, wherein the low spot determining step comprises measuring a height of the infill particulate material and comparing the measured height to a desired or nominal height of the infill particulate material.

11. The method of claim 10, further including allowing a user to input the desired or nominal height of the infill particulate material for use in the low spot determining step.

12. A method for measuring a turf infill profile of an infill particulate material lying on a backing material of a synthetic turf surface and for adding infill particulate material to low spots in the turf infill profile, which comprises:
    (a) providing a measurement assembly including one or both of a probe for measuring the turf infill profile at a plurality of sampled locations in the synthetic turf surface and an optical sensor for measuring an amount of visible infill particulate and an amount of visible backing material;
    (b) providing a top dresser that carries a supply of infill particulate material and that is capable of applying additional infill particulate material to the synthetic turf surface;
    (c) moving the measurement assembly over the synthetic turf surface and determining if low spots exist in the turf infill profile based on one or both of the sampled locations and locations where a ratio of the amount of visible infill particulate to the amount of visible backing material is below a programmed value; and (d) moving the top dresser over the synthetic turf surface and, for the locations at which low spots have been determined to exist, operating the top dresser to apply additional infill particulate material to the low spots.

13. The method of claim 12, wherein the measurement assembly and the top dresser are moved in concert with one another over the synthetic turf surface, and wherein operating the top dresser to apply additional infill particulate material to any given low spot occurs substantially simultaneously with the determination by the measurement assembly that the given low spot is present.

14. The method of claim 12, wherein the step of providing a top dresser includes providing a vehicle including the top dresser and wherein the step of providing a measurement assembly includes providing a mobile measurement apparatus operably coupled to the vehicle.

15. The method of claim 13, wherein the low spot determining step comprises measuring a height of the infill particulate material and comparing the measured height to a desired or nominal height of the infill particulate material.

16. The method of claim 15, further including allowing a user to input the desired or nominal height of the infill particulate material for use in the low spot determining step.

* * * * *